US008133221B2

(12) United States Patent
Malecki et al.

(10) Patent No.: US 8,133,221 B2
(45) Date of Patent: Mar. 13, 2012

(54) ENERGY BASED DEVICES AND METHODS FOR TREATMENT OF ANATOMIC TISSUE DEFECTS

(75) Inventors: William Malecki, San Francisco, CA (US); Dan Francis, Mountain View, CA (US); Kenneth Horne, San Francisco, CA (US); Mark E. Deem, Mountain View, CA (US); Hanson Gifford, Woodside, CA (US); Jose Alejandro, Sunnyvale, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1243 days.

(21) Appl. No.: 11/771,528

(22) Filed: Jun. 29, 2007

(65) Prior Publication Data

US 2007/0287999 A1 Dec. 13, 2007

Related U.S. Application Data

(62) Division of application No. 10/952,492, filed on Sep. 27, 2004, now Pat. No. 7,367,975.

(51) Int. Cl.
*A61B 18/14* (2006.01)
(52) U.S. Cl. .......................................... 606/41; 606/49
(58) Field of Classification Search .................. 606/27, 606/28, 41, 45–50
See application file for complete search history.

(56) References Cited

U.S. PATENT DOCUMENTS

| 2,275,167 A | 3/1942 | Bierman |
| 2,580,628 A | 1/1952 | Welsh |
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |

(Continued)

FOREIGN PATENT DOCUMENTS

EP           135840 A2       4/1985

(Continued)

OTHER PUBLICATIONS

Anzola et al., "Potential Source of Cerebral Embolism in Migraine with Aura," *Neurology* (1999) 52(8): 1622.

(Continued)

*Primary Examiner* — Michael Peffley
(74) *Attorney, Agent, or Firm* — Oblon, Spivak, McClelland, Maier & Neustadt, L.L.P.

(57) ABSTRACT

Methods for treating anatomic tissue defects such as patent foramen ovale (PFO) generally involve positioning a distal end of an elongate catheter device at the site of the anatomic defect, exposing an expandable housing and energy transmission member out of the distal end of the catheter device, engaging the housing with tissues at the site of the anatomic defect, applying suction to the tissues via the housing to bring the tissues together; and applying energy to the tissues with the energy transmission member to substantially close the anatomic defect acutely. Apparatus generally include an elongate catheter body, a housing extending from a distal end of the catheter body for engaging tissues at the site of the anatomic defect, and an energy transmission member adjacent a distal end of the housing, the energy transmission member having at least one substantially planar surface.

22 Claims, 32 Drawing Sheets

U.S. PATENT DOCUMENTS

| | | | |
|---|---|---|---|
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliot et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,562,720 A * | 10/1996 | Stern et al. ................. 607/98 |
| 5,569,239 A | 10/1996 | Sinofsky |
| 5,571,216 A | 11/1996 | Anderson |
| 5,575,772 A | 11/1996 | Lennox |
| 5,584,872 A | 12/1996 | Lafontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,693,078 A | 12/1997 | Desai et al. |
| 5,709,224 A | 1/1998 | Behl |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier |
| 6,063,085 A | 5/2000 | Tay |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | Lafontaine |
| 6,211,335 B1 | 4/2001 | Owen et al. |
| 6,221,068 B1 | 4/2001 | Fried et al. |
| 6,236,875 B1 | 5/2001 | Bucholz |
| 6,254,600 B1 * | 7/2001 | Willink et al. ................. 606/41 |
| 6,257,241 B1 | 7/2001 | Wampler |
| 6,283,961 B1 * | 9/2001 | Underwood et al. ........... 606/41 |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,364,876 B1 * | 4/2002 | Erb et al. ......................... 606/33 |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysee et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,529,778 B2 * | 3/2003 | Prutchi ......................... 607/119 |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 * | 6/2003 | Francischelli et al. .......... 607/98 |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman |
| 6,669,693 B2 | 12/2003 | Friedman |
| 6,676,685 B2 | 1/2004 | Pedros et al. |
| 6,682,546 B2 | 1/2004 | Amplatz |
| 6,692,450 B1 | 2/2004 | Coleman |
| 6,702,835 B2 | 3/2004 | Ginn |
| 6,712,804 B2 | 3/2004 | Roue et al. |
| 6,712,836 B1 | 3/2004 | Berg et al. |
| 6,716,211 B2 | 4/2004 | Mulier et al. |
| 6,726,718 B1 | 4/2004 | Carlyle et al. |
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |

| | | |
|---|---|---|
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns et al. |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 | 9/2005 | Malecki et al. |
| 6,946,134 B1 | 9/2005 | Rosen et al. |
| 6,960,205 B2 | 11/2005 | Jahns et al. |
| 7,025,756 B2 | 4/2006 | Frazier et al. |
| 7,094,215 B2 | 8/2006 | Davison et al. |
| 7,165,552 B2 | 1/2007 | Deem et al. |
| 7,238,182 B2 | 7/2007 | Swoyer et al. |
| 7,367,975 B2 | 5/2008 | Malecki et al. |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Markin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1 | 12/2004 | Auth |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | Mcintosh |
| 2005/0075665 A1 | 4/2005 | Brenzel et al. |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0131401 A1 | 6/2005 | Malecki et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2006/0271030 A1 | 11/2006 | Francis et al. |
| 2006/0271040 A1 | 11/2006 | Horne et al. |
| 2007/0088355 A9 | 4/2007 | Auth |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| JP | 2003-510126 | 3/2003 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/23959 A1 | 5/1999 |
| WO | WO 99/49788 A | 10/1999 |
| WO | WO 00/07506 A2 | 2/2000 |
| WO | WO 00/09027 A1 | 2/2000 |
| WO | WO 01/13810 A1 | 3/2001 |
| WO | WO 01/22897 | 4/2001 |
| WO | WO 01/78596 A1 | 10/2001 |
| WO | WO 01/82778 A | 11/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 A2 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 2004/043266 A2 | 5/2004 |
| WO | WO 2004/069055 A2 | 8/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/074814 A2 | 8/2005 |
| WO | WO 2005/046487 A1 | 12/2005 |
| WO | WO 2005/115256 A | 12/2005 |

OTHER PUBLICATIONS

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

Besio et al., "Quantizing the Depth of Bioelectrical Sources for Non-Invasive 3D Imaging," *IJBEM*, vol. 7, No. 2, (2005), 4 pages total.

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electorode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Fenner et al., "Shear Strength of Tissue Bonds as a Function of Bonding Temperature: A Proposed Mechanism for Laser-Assisted Tissue Welding," *Laser in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Olson et al., "Developing an Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; 1985:1582-1586.

Polgar et al., "Comparison of Two Different Techniques for Closed-Chest His Bundle *Ablation*," In: *Perez Gomez F, ed*. Cardiac Pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Poppas et al., "Temperature-Controlled Laser Photocoagulation of Soft Tissue: in Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

\* cited by examiner

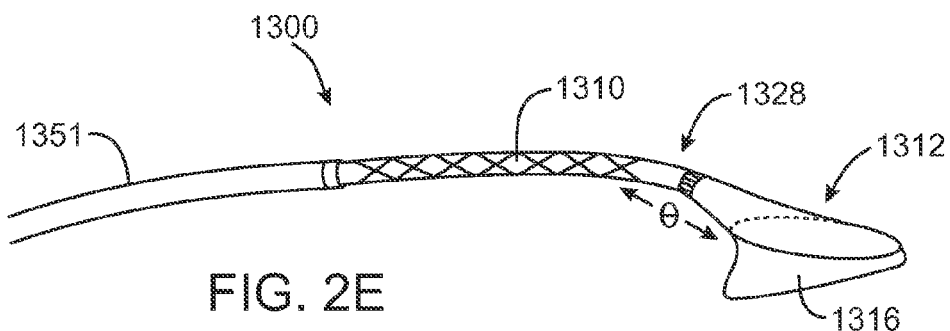
FIG. 2E
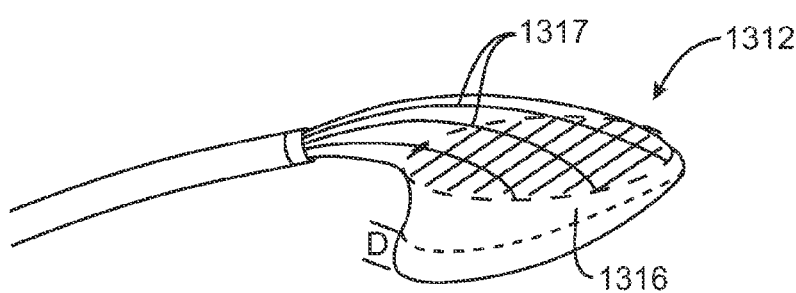
FIG. 2F
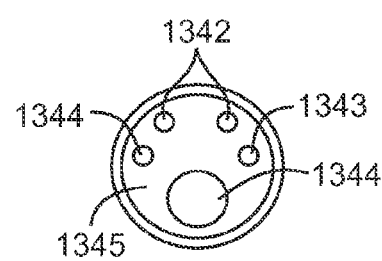
FIG. 2G"A
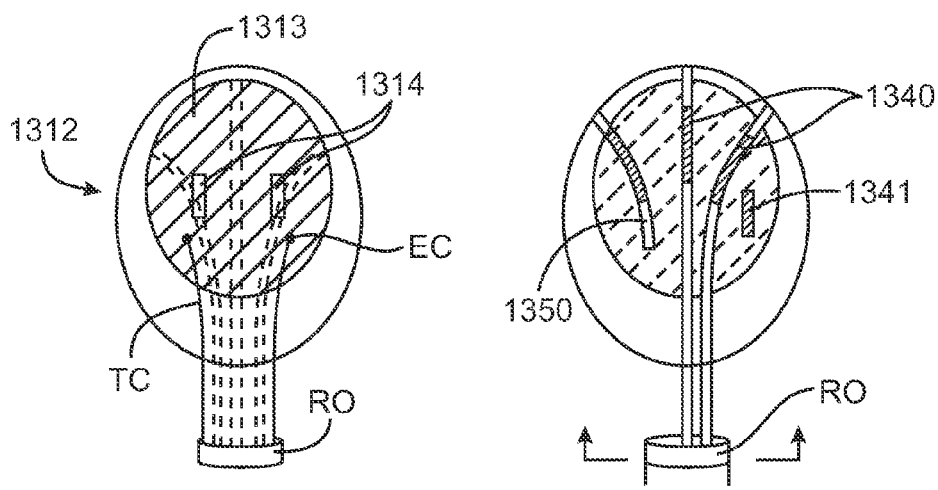
FIG. 2G'
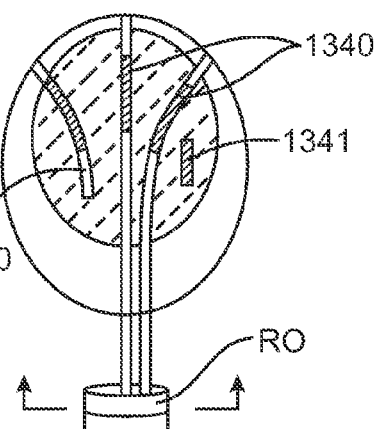
FIG. 2G"

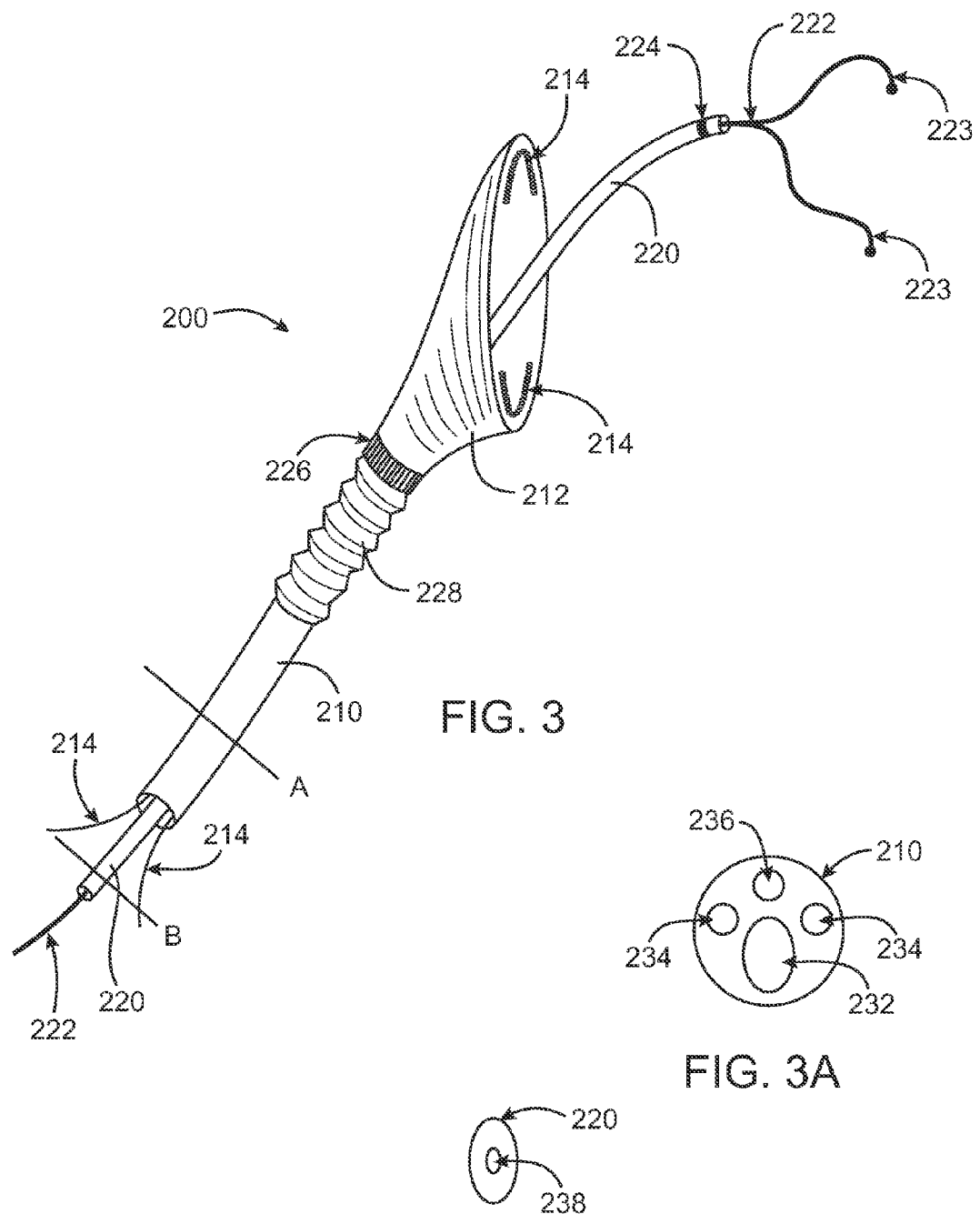

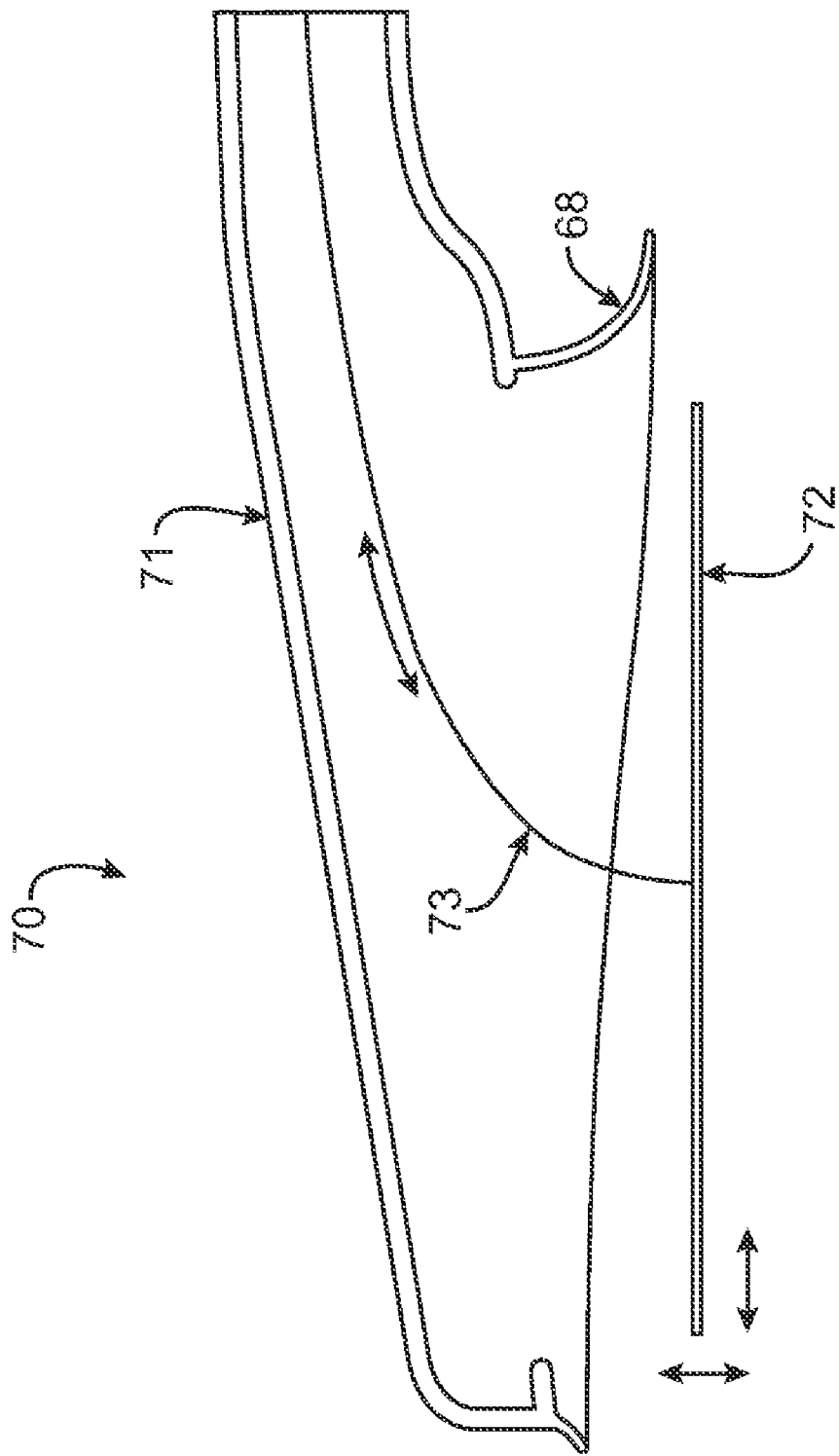

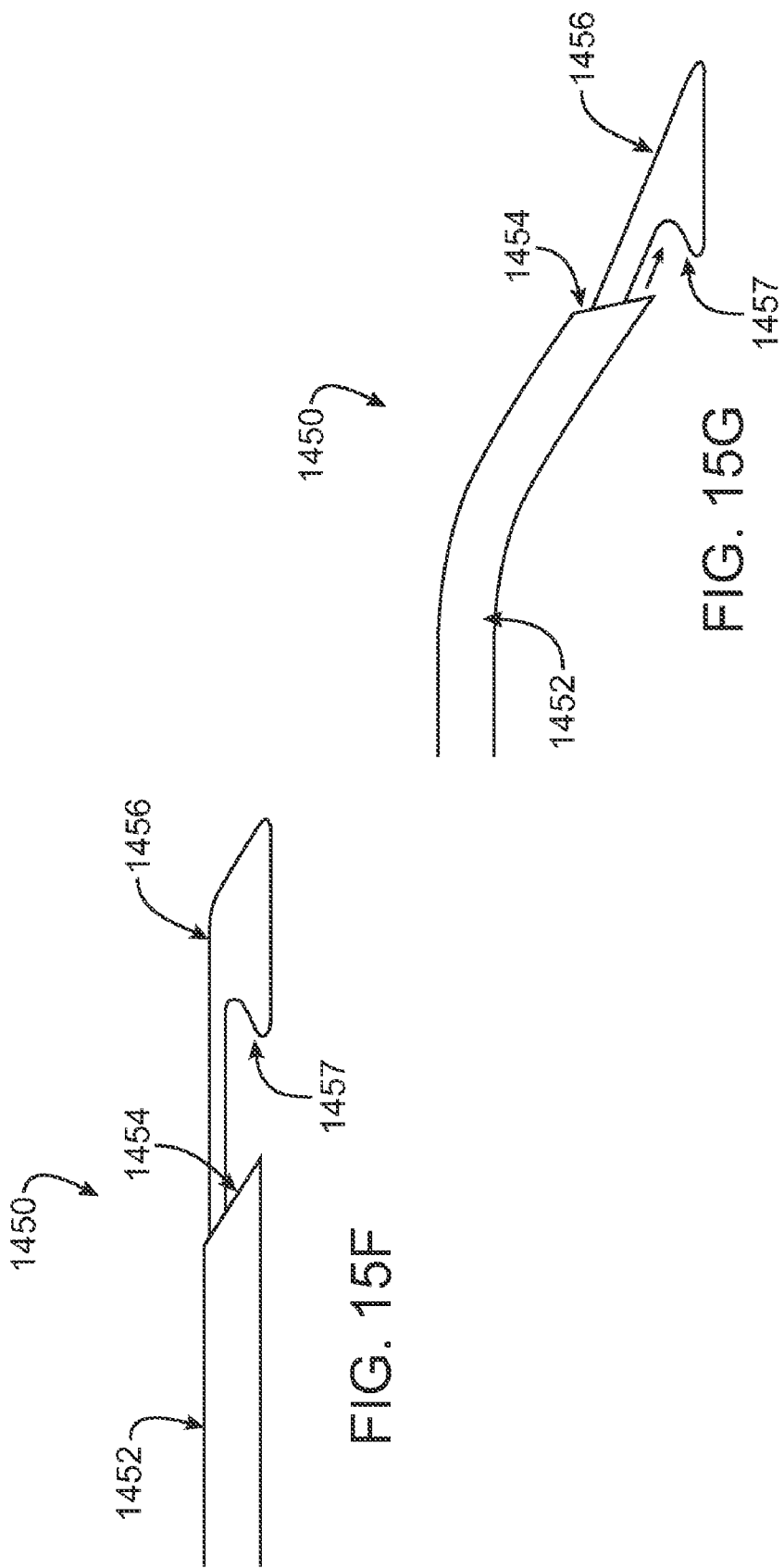

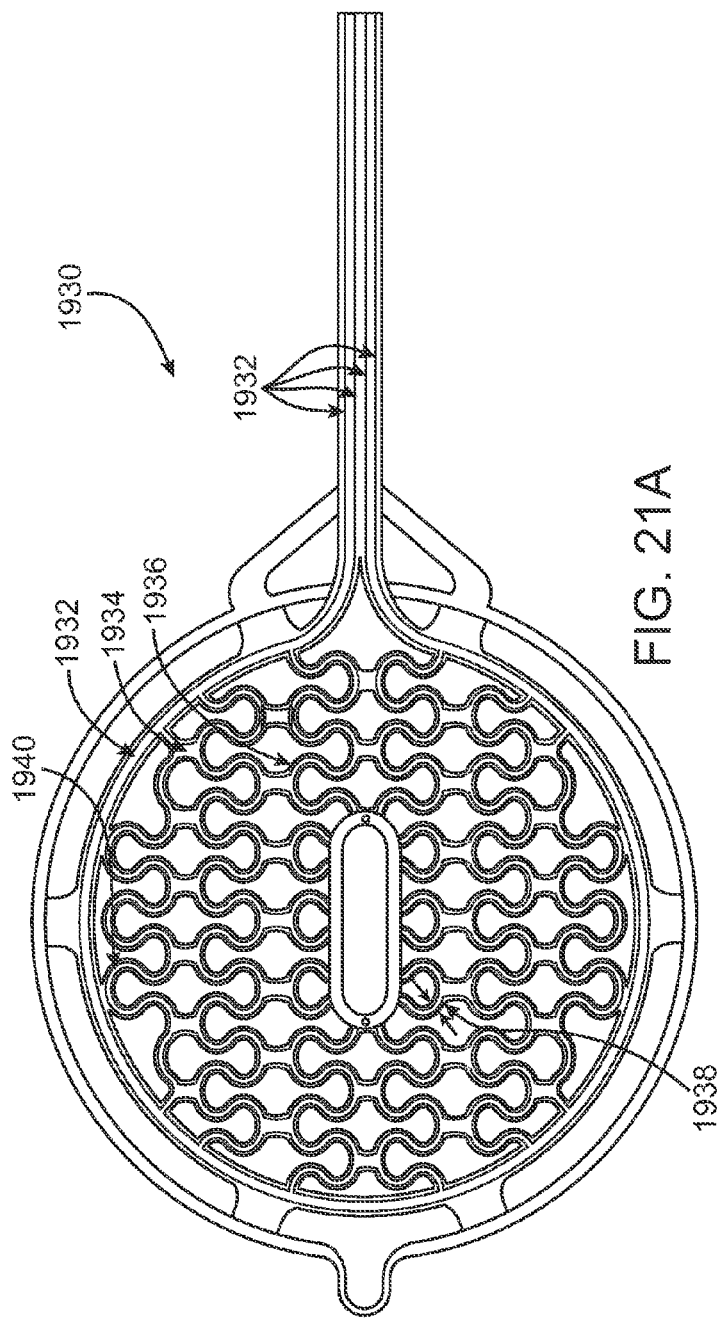
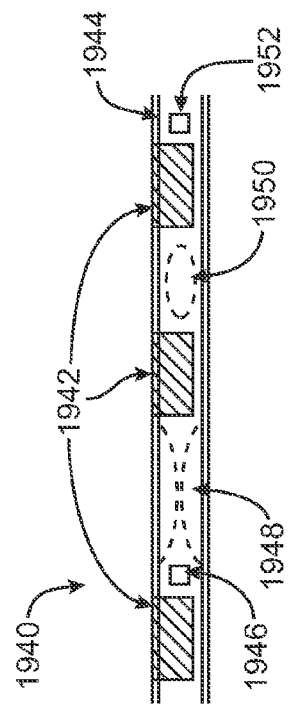

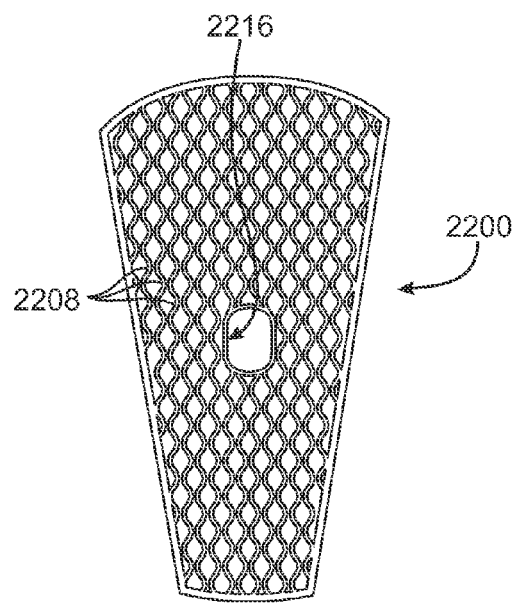
FIG. 24A
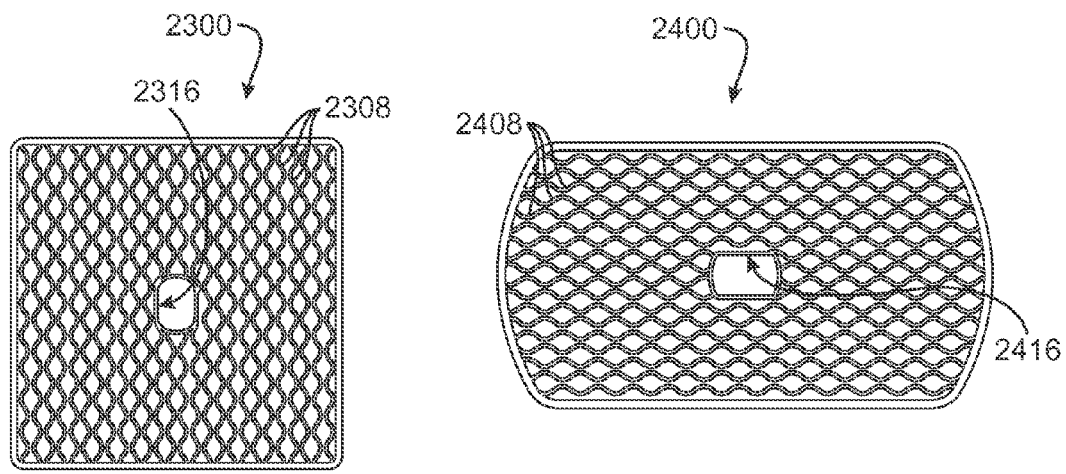
FIG. 24B
FIG. 24C

ENERGY BASED DEVICES AND METHODS FOR TREATMENT OF ANATOMIC TISSUE DEFECTS

CROSS-REFERENCES TO RELATED APPLICATIONS

This application is a divisional of U.S. patent application Ser. No. 10/952,492, filed Sep. 27, 2004, U.S. Pat. No. 7,367, 975, which is related to U.S. patent application Ser. No. 10/873,348, filed Jun. 21, 2004, U.S. Pat. No. 7,293,562, which is a continuation-in-part of U.S. patent application Ser. No. 10/679,245, filed Oct. 2, 2003, U.S. Pat. No. 6,939,348, which claims priority to U.S. Provisional Patent Application Nos. 60/458,854, filed on Mar. 27, 2003; 60/478,035, filed on Jun. 11, 2003, and 60/490,082, filed on Jul. 24, 2003. The full disclosures of all of the above-listed patent applications are hereby incorporated by reference.

BACKGROUND OF THE INVENTION

The invention generally relates to medical devices and methods. More specifically, the invention relates to energy based devices and methods for treatment of anatomic defects in human tissue, such as patent foramen ovale (PFO), atrial septal defect (ASD), ventricular septal defect (VSD), patent ductus arteriosis (PDA), left atrial appendages (LAA), blood vessel wall defects and certain electrophysiological defects.

The following is an example of how one particular type of anatomical defect—a PFO—is formed. Fetal blood circulation is very different from adult circulation. Because fetal blood is oxygenated by the placenta, rather than the fetal lungs, blood is generally shunted past the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium. A patent ductus arteriosis (PDA) is a tubular communication between the pulmonary artery and the aorta, which typically closes shortly after birth.

Patent foramen ovale has long been considered a relatively benign condition, since it typically has little effect on the body's circulation. More recently, however, it has been found that a significant number of strokes may be caused at least in part by PFOs. In some cases, a stroke may occur because a PFO allows blood containing small thrombi to flow directly from the venous circulation to the arterial circulation and into the brain, rather than flowing to the lungs where the thrombi can become trapped and gradually dissolved. In other cases, a thrombus might form in the patent channel of the PFO itself and become dislodged when the pressures cause blood to flow from the right atrium to the left atrium. It has been estimated that patients with PFOs who have already had cryptogenic strokes may have a risk of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headache—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for defect closure are generally fairly invasive and/or have potential drawbacks. One strategy is simply to close a defect during open heart surgery for another purpose, such as heart valve surgery. This can typically be achieved via a simple procedure such as placing a stitch or two across the defect with vascular suture. Performing open heart surgery purely to close an asymptomatic PFO or even a very small ASD, however, would be very hard to justify.

A number of interventional devices for closing defects percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the defect. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO and other defects impractical. Additionally, currently available devices typically close a PFO by placing material on either side of the tunnel of the PFO, compressing and opening the tunnel acutely, until blood clots on the devices and causes flow to stop.

Research into methods and compositions for tissue welding has been underway for many years. Of particular interest are technologies developed by McNally et.al., (as shown in U.S. Pat. No. 6,391,049) and Fusion Medical (as shown in U.S. Pat. Nos. 5,156,613, 5,669,934, 5,824,015 and 5,931, 165). These technologies all disclose energy delivery to tissue solders and patches to join tissue and form anastamoses between arteries, bowel, nerves, etc. Also of interest are a number of patents by inventor Sinofsky, relating to laser suturing of biological materials (e.g., U.S. Pat. Nos. 5,725, 522, 5,569,239, 5,540,677 and 5,071,417). None of these disclosures, however, show methods or apparatus suitable for positioning the tissues of an anatomic defect for welding or for delivering the energy to an anatomic defect to be welded.

Causing thermal trauma to a patent ovale has been described in two patent applications by Stambaugh et al. (PCT Publication Nos. WO 99/18870 and WO 99/18871). The devices and methods described, however, cause trauma to PFO tissues to hopefully eventually cause scar tissue formation which will close the PFO. In addition, Blaeser et al. (US Patent Publication US2003/0208232), further describes causing trauma, or abrading, and holding the abraded tissue in apposition to allow the tissue to heal together. Using such devices and methods, the PFO typically remains patent immediately after the procedure, or abrasion, and only closes sometime later, or is treated and then held together to heal over time. Frequently, scar tissue may fail to form or may form incompletely, resulting in a still patent PFO.

In addition to PFO, a number of other anatomic tissue defects, such as other ASDs, ventricular septal defects (VSDs), patent ductus arteriosis (PDA), aneurysms and other blood vessel wall defects, atrial appendages and other naturally occurring cavities within which clot can form, and the like cause a number of different health problems (note that the term "defect" may include a naturally occurring structure that results a potential health risk such as the clot forming in the atrial appendage). U.S. Patent Application No. 2004/0098031 (Van der Burg), and U.S. Pat. Nos. 6,375,668 (Gifford) and 6,730,108 (Van Tassel et al.), the full disclosures of which are incorporated herein by reference, disclose a variety of techniques and devices for treating anatomic defects. In addition, the inventors of the present invention have described a number of improved devices, methods and systems for treating PFO, many of which may be adapted for treating other anatomic tissue defects as well. For example, related patent applications assigned to the assignee of the present invention include U.S. patent application Ser. Nos. 10/665,974, filed on Sep. 16, 2003; 10/679,245, filed Oct. 2, 2003; 10/787,532, filed Feb. 25, 2004; and 10/811,228, filed Mar. 26, 2004, the full disclosures of which are incorporated herein by reference.

Despite improvements made thus far, it would be advantageous to have even further improved methods and apparatus for treating anatomic tissue defects such as PFOs and the other anatomic structures mentioned above. Ideally, such methods and apparatus would help seal an anatomic tissue defect during, immediately after or soon after performing a treatment procedure. Also, such devices and methods would leave no foreign material (or very little material) in a patient's heart. Furthermore, such methods and apparatus would preferably be relatively simple to manufacture and use, thus rendering prophylactic treatment of PFO and other tissue defects a viable option. In addition, based upon the unique characteristics of the devices of the present invention, such devices may also be employed for treating certain electrophysiological defects, such as atrial fibrillation, supraventricular tachacardia (SVT), atrial flutter, A-V node re-entry, and Wolf Parkinson White syndrome. At least some of these objectives will be met by the present invention.

BRIEF SUMMARY OF THE INVENTION

The present invention generally provides devices and methods for treating anatomic defects in human tissues, such as patent foramen ovale (PFO), atrial septal defect, ventricular septal defect, patent ductus arteriosis, left atrial appendages, and blood vessel wall defects. In one aspect of the present invention, apparatus for treating an anatomic defect in a heart includes an elongate catheter body having a proximal end and a distal end, a housing extending from the distal end of the catheter body for engaging tissues at the site of the anatomic defect, and an energy transmission member adjacent a distal end of the housing. The energy transmission member has at least one substantially planar surface, and the housing is adapted to apply vacuum to the tissues to bring them together and position them against the energy transmission member. In various embodiments, the anatomic defect may be any suitable tissue defect, such as but not limited to those listed above. The following description will often focus on PFO treatment, but various embodiments may be employed for treating any other suitable tissue defect.

In some embodiments, the apparatus also includes a sheath disposed over at least part of the catheter body and having a proximal end and a distal end. In such embodiments, the energy transmission member and the housing are collapsible and axially movable relative to the sheath, from a collapsed position within the sheath to an expanded position beyond the distal end of the sheath. Optionally, the sheath may include a bend, closer to its distal end than its proximal end. In some embodiments, the catheter body also includes a bend, closer to its distal end than a proximal end of the sheath. In such embodiments, the catheter body bend and the sheath bend allow a user to change an angle of orientation of the energy transmission member and the housing by moving the catheter body relative to the sheath. Optionally, the sheath may also include a stretchable distal end for facilitating movement of the housing and the energy transmission member from the expanded configuration to the collapsed configuration within the sheath.

The phrase "tissues adjacent an anatomic defect," for the purposes of this application, means any tissues in, around or in the vicinity of an anatomic defect which may be used or manipulated to help close the anatomic defect, or decrease viability of tissue conduction, such as in ablation for electrophysiological defects. For example, tissues adjacent a PFO include septum primum tissue, septum secundum tissue, atrial septal tissue lateral to the septum primum or septum secundum, tissue within the tunnel of the PFO, tissue on the right atrial surface or the left atrial surface of the atrial septum and the like.

In various embodiments, any of a number of energy transfer devices and forms of energy may be used to provide energy transfer. Types of energy used may include, for example, radiofrequency energy, cryogenic energy, laser energy, ultrasound energy, resistive heat energy, microwave energy and the like. Application of energy to tissues to substantially close the anatomic defect acutely may sometimes be referred to as "tissue welding." Preferably, tissue welding methods of the present invention will be performed without using tissue soldering material or other foreign material. In some embodiments, however, it may be advantageous to use one or more solder materials. Various solders and other tissue soldering matrices are described more fully in U.S. patent application Ser. No. 10/665,974, which was previously incorporated by reference. Examples of tissue solders or adhesives which may be used include, but are not limited to, autologous blood, albumin, collagen, fibrin, cyanoacrylates, mussel byssus adhesives, polymer hot melt adhesives and the like.

In various embodiments, tissues may be brought together (or "apposed") before, during and/or after application or removal of energy to the tissues. Generally, energy application or removal will act to denature collagen in the anatomic defect tissues. If the tissues are apposed before and/or during denaturation and/or after denaturation, the collagen in once-separated tissues binds together to bring the tissues together. Therefore, various embodiments of the invention include one or more devices for bringing (and possibly holding) tissues together before, during and/or after energy application or removal. Such devices include, for example, tissue covering members, which may also be suction or vacuum application members, expandable members for insertion and expansion within an anatomic defect, distal tip members for contacting a left atrial surface of PFO tissue and the like.

In some embodiments, the housing includes a narrow proximal end coupled with the distal end of the catheter body and a flared distal end. Optionally, the housing may also include a flexible, cylindrical foot extending from the flared distal end for contacting the tissues. In some embodiments, the housing and the flexible foot comprise different materials, while in others they are made of the same material. In one embodiment, the flexible foot extends laterally from the flared distal end to have a larger diameter than a diameter of the flared distal end. In some embodiments, the electrode is movable relative to the housing to allow for a lower profile device, and alternatively to apply energy to the tissues at multiple locations within the larger diameter of the flexible foot without re-acquiring the targeted region. The flared distal end of the housing may have any suitable shape, such as but not limited to circular, ovoid, elliptical, rectangular, triangular, pentagonal, hexagonal, octagonal, crescent-shaped or fan-shaped.

In various embodiments, the housing may comprise any suitable material or combination of materials, typically selected to give the housing a degree of resiliency, to allow it to collapse for housing within a catheter sheath and to expand when exposed out of the distal end of the sheath. For example, materials used to manufacture the housing may include but are not limited to PET, DACRON®, other polyesters, polypropylene, PTFE, ePTFE, PEEK, nylon, polyurethane, polyethylene, silicone, urethane or metal. In some embodiments, the housing further comprises a lubricious coating over at least part of its outer surface. Optionally, the housing may further include at least one supportive strut for preventing complete collapse of the housing when vacuum is applied to the tissues. In some embodiments, the housing and the strut(s) comprise the same material, while in others they are made of different materials. The housing may also optionally include at least one radiopaque marker or radiopaque material.

In some embodiments, the catheter device further includes an irrigation tube extending through the catheter body and having a distal aperture disposed within the housing and a vacuum tube extending through the catheter body and having a distal aperture disposed within the housing. In one embodiment, an inner surface of the housing includes a plurality of ridges and valleys forming channels to direct irrigation fluid from the irrigation tube distal aperture toward the tissues and subsequently toward the vacuum tube distal aperture. The inner surface may optionally further include an irrigation fluid blocking surface feature to help direct fluid forward and away from the irrigation tube distal aperture. In some embodiments, the irrigation tube is adapted to allow passage of a guidewire therethrough.

In some embodiments, the at least one energy transmission member comprises a planar radiofrequency energy electrode disposed adjacent the distal end of the housing. In one embodiment, the electrode is axially movable in and out of the distal end of the housing. Alternatively, the electrode may be directly attached to the housing. In various embodiments, the planar surface electrode may have any suitable shape, such as but not limited to circular, ovoid, elliptical, rectangular, triangular, pentagonal, hexagonal, octagonal, crescent-shaped or fan-shaped.

In some embodiments, the planar surface electrode includes an outer rim extending at least partially around an outer circumference of the electrode and a plurality of metallic struts formed in a pattern within the outer rim. In one embodiment, the rim is discontinuous, thus enhancing collapsibility of the electrode. In other embodiments, the rim includes one or more inward bends directed toward the struts, the inward bends adapted to promote collapsibility of the electrode. In some embodiments, some of the struts are attached to other struts as well as to the outer rim. In other embodiments, the struts are attached only to the outer rim and not to one another. In other embodiments, the struts are not attached at all to the outer rim, and may be attached to the housing through the material of the housing or other structure. The pattern of struts may include at least one area of more closely positioned struts relative to another area of less closely positioned struts, such that different areas of the electrode provide different amounts of energy transmission to the tissues. Alternatively or additionally, the pattern of struts may include at least one area of thicker struts relative to another area of thinner struts, such that different areas of the electrode provide different amounts of energy transmission to the tissues.

In some embodiments, the pattern of struts includes at least one fold line along which the electrode folds to allow the electrode to collapse. In some embodiments, the struts are attached asymmetrically to the outer rim such that a first half of the housing and electrode folds into a second half of the housing and electrode when the housing and electrode assume their collapsed configurations. For example, in some embodiments, the struts are attached to the outer rim at between 8 and 16 attachment points to enhance collapsibility of the electrode.

In some embodiments, the device further includes a plurality of metallic attachment members extending from the outer rim for attaching the electrode to the housing. For example, the plurality of attachment members may include an inferior attachment member for attaching proximally to an inferior portion of the housing and multiple superior attachment members for attaching proximally to a superior portion of the housing. In one embodiment, the inferior attachment member extends onto an inferior portion of the catheter body, and the superior attachment members extend onto a superior portion of the catheter body. In one embodiment, the inferior attachment member divides before attaching to the outer rim at two attachment points. In an alternative embodiment, the inferior attachment member curves asymmetrically before attaching to the outer rim. In some embodiments, the struts are attached to the outer rim at locations apart from attachment points of the attachment members to the outer rim. Alternatively, the struts may be attached to the outer rim at attachment points of the attachment members to the outer rim.

In various embodiments, an electrode may include any of a number of additional features. For example, in some embodiments, the electrode further comprises at least one guidewire aperture to allow passage of a guidewire through the electrode. The guidewire aperture may be disposed along the electrode in an offset position to facilitate positioning of the electrode over the anatomic defect. Some embodiments include two offset guidewire apertures for facilitating positioning of the electrode over the anatomic defect. Some embodiments further include a thermocouple attached to the electrode.

In some embodiments, the energy transmission member comprises a radiofrequency electrode having multiple planar surfaces connected by one or more bends, such as a "stepped" electrode. For example, such an electrode may have a first planar surface, a bend, and a second planar surface. Such configuration may help promote contact of the electrode with asymmetrical anatomic tissues and tissue defects. Optionally, the housing may also have such a stepped, or "multiplanar," configuration that matches that of the electrode. In yet another embodiment, the energy transmission member may comprise a planar, expandable, braided wire electrode.

In another aspect of the present invention, a method of treating an anatomic defect in human tissue involves: positioning a distal end of an elongate catheter device at the site of the anatomic defect; exposing an expandable housing and energy transmission member out of the distal end of the catheter device; engaging the housing with tissues at the site of the anatomic defect; applying suction to the tissues via the housing to bring the tissues together; and applying energy to the tissues with the energy transmission member to substantially close the anatomic defect acutely. In one embodiment, the method further involves repositioning the housing and the energy transmission member within the catheter device and removing the catheter device from the site of the anatomic defect.

By "substantially," it is meant that a stable tissue bridge will be formed across the anatomic defect, which will withstand physiologic pressures. A substantially closed anatomic defect, however, may still have one or more small gaps or openings, which will in at least some cases close over time via the healing process. By "acutely," it is meant that the anatomic defect is substantially closed when the closure procedure is completed. Thus, acute closure distinguishes devices and methods of the present invention from prior protocols, which rely on delayed anatomic defect closure via tissue healing and scarring. "Acutely," for purposes of this application, does not mean temporarily, since devices and methods of the present invention will typically provide for permanent (or at least long-term) anatomic defect closure.

In some embodiments, exposing and repositioning the housing and the energy transmission member involve moving a sheath of the catheter device relative to a catheter body of the catheter device. For example, repositioning the housing and the energy transmission member may involve advancing the sheath and/or retracting the catheter body to cause the housing and the energy transmission member to collapse as they enter the sheath. In some embodiments, the housing and energy transmission member collapse along one or more lines of structural weakness adapted to promote collapsibility. In some embodiments, collapsing of the housing and energy transmission member comprises one lateral side of the housing and energy transmission member folding over an opposite lateral side.

Optionally, the method may further involve passing fluid out of an irrigation fluid aperture in the housing and suctioning the fluid back into a suction aperture in the housing. In some embodiments, the method may further comprise directing the fluid, via multiple channels on an inner surface of the housing, away from the irrigation fluid aperture and toward the suction aperture. Alternatively, the multiple channels could be used to direct the irrigation fluid away from the fluid aperture and over targeted areas of the electrode to cool the electrode, wholly or in selected regions, to prevent the electrode from adhering to the tissue. Some embodiments also include monitoring the suctioned fluid to determine the blood content of the fluid. Alternatively or additionally, a flow rate of fluid from a fluid supply reservoir into the catheter may be monitored to determine whether a seal has been formed.

In some embodiments, engaging the housing with the tissues automatically engages the energy transmission member with the tissues. In other embodiments, applying suction to the tissues automatically engages the energy transmission member with the tissues. Still other embodiments further involve moving the energy transmission member relative to the housing to engage the energy transmission member with the tissues. These latter embodiments may optionally also involve repositioning the energy transmission member relative to the housing to engage the tissues at a different location.

The energy applied to the tissues may include, but is not limited to, radiofrequency, microwave, ultrasound, laser, heat and/or cryogenic energy. In some embodiments, the energy is applied at different levels to different areas of tissue via the energy transmission member. For example, the different levels of energy may be applied via different densities of material comprising the energy transmission member. In other embodiments, the different levels of energy are applied via multiple energy delivery devices coupled with the energy transmission member at different regions of the ETM. In addition, in some embodiments it may be advantageous to heat the electrode prior to applying it to tissue, to facilitate the application of higher temperatures to the surface of the defect to be treated, as in direct heating versus use of RF, which relies on conductive or inductive heating of tissue at some depth below the surface.

These and other embodiments are described in further detail in the following description related to the appended drawing figures.

BRIEF DESCRIPTION OF THE DRAWING FIGURES

FIG. 2E is a side view of a distal end of a catheter device for treating an anatomic tissue defect, including a curved reinforced catheter shaft according to one embodiment of the present invention;

FIG. 2F is a side view of a distal end of a catheter device for treating an anatomic tissue defect according to an embodiment of the present invention, including an electrode and an electrode housing with struts according to one embodiment of the present invention;

Figure 4:
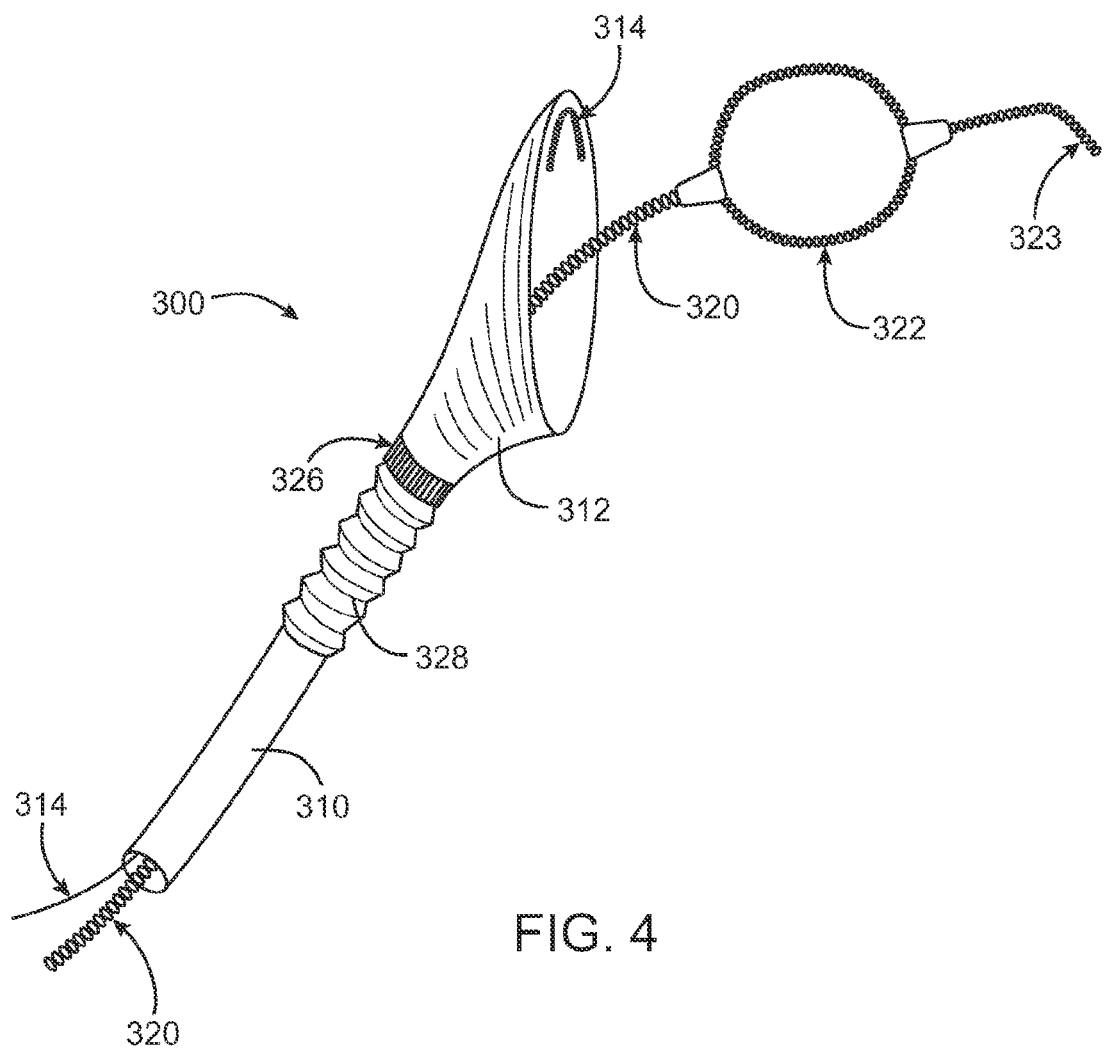
Figure 5:
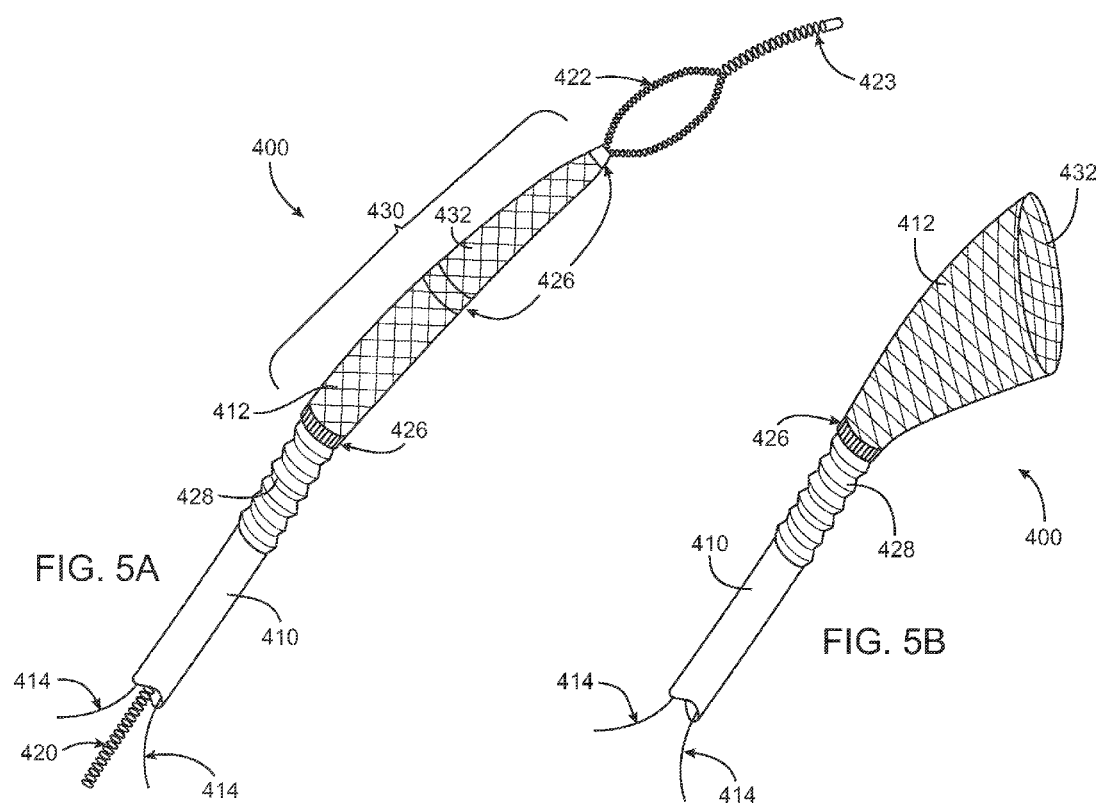
Figure 6:
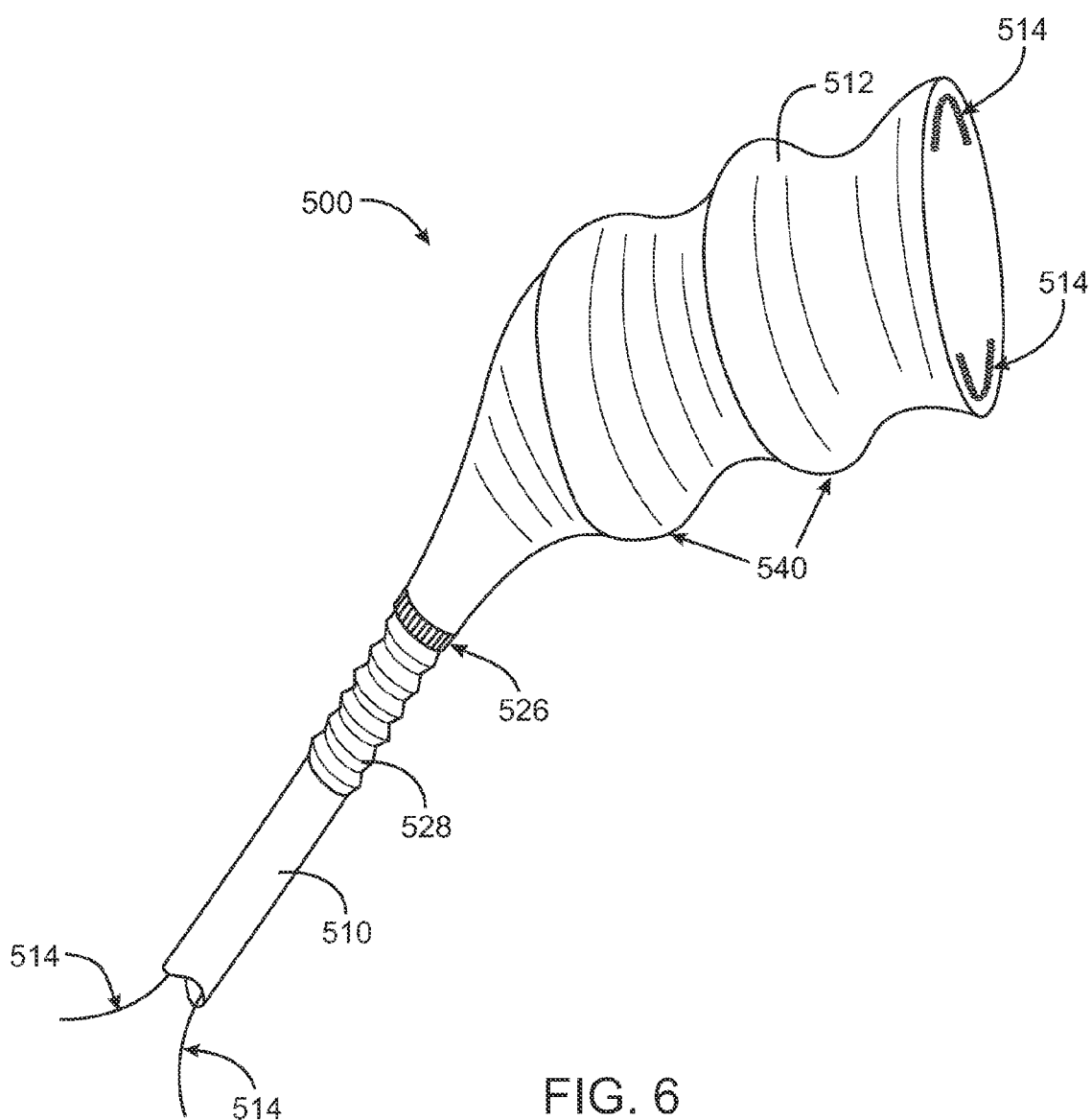
Figure 7:
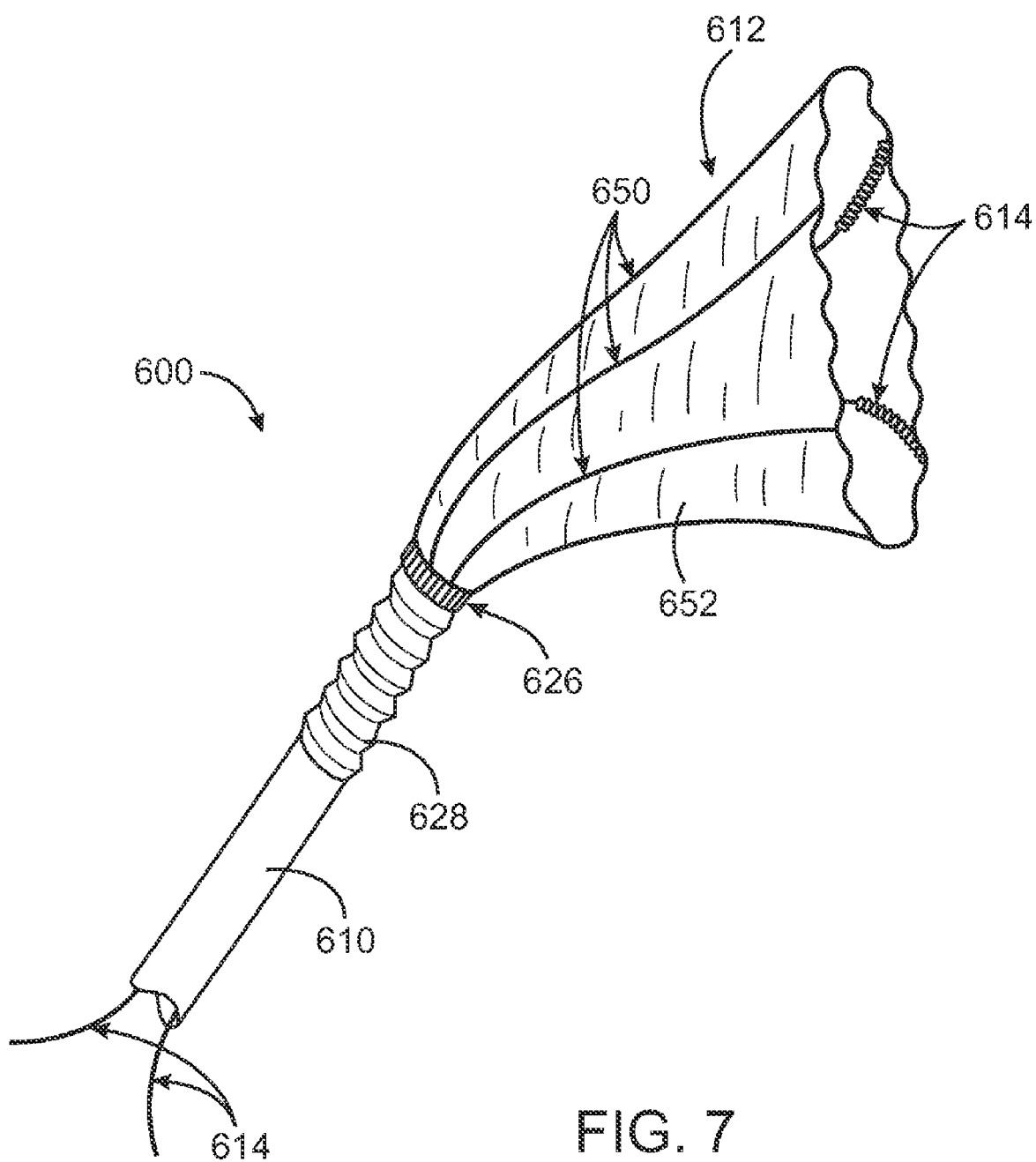
Figure 10:
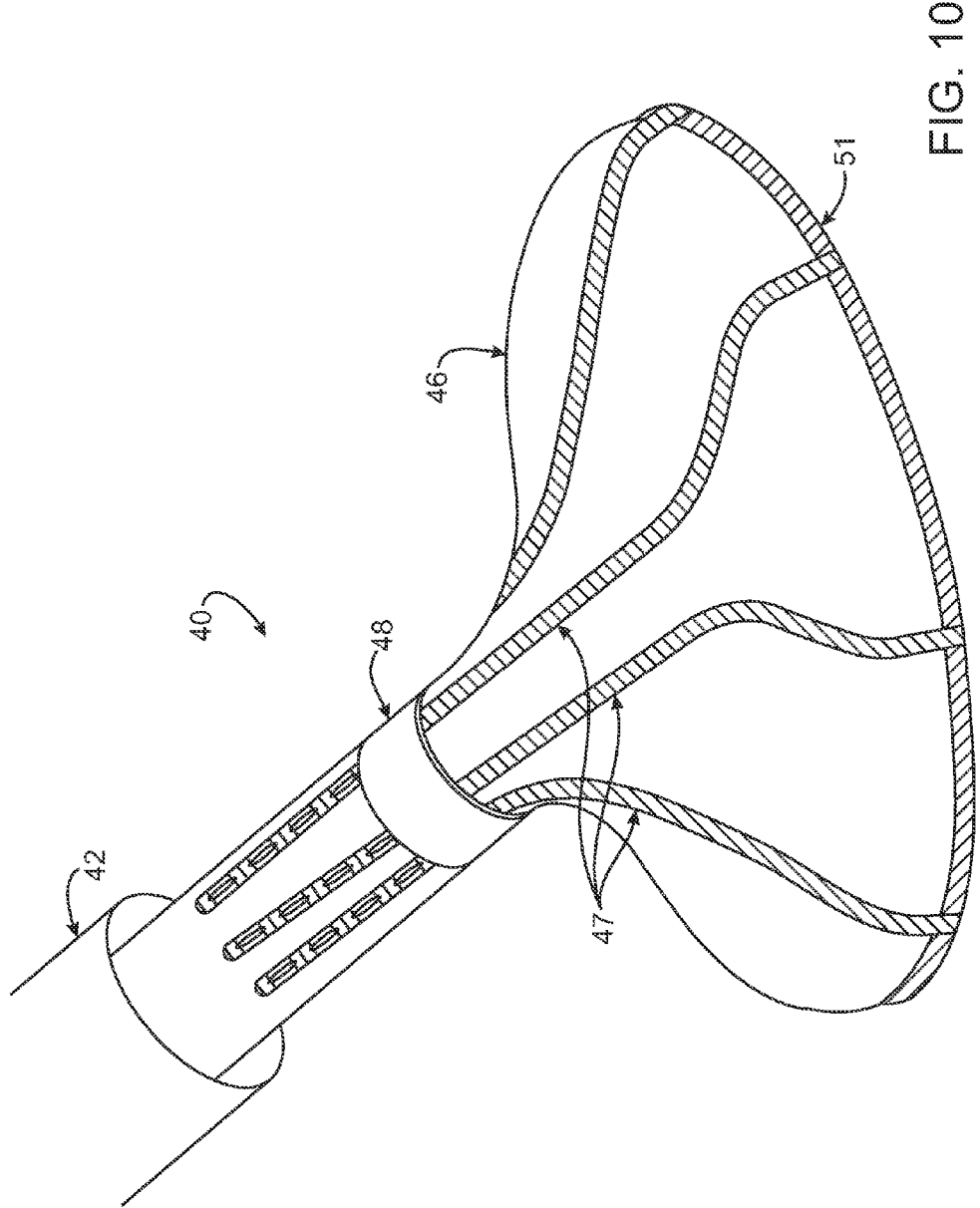
Figure 11:
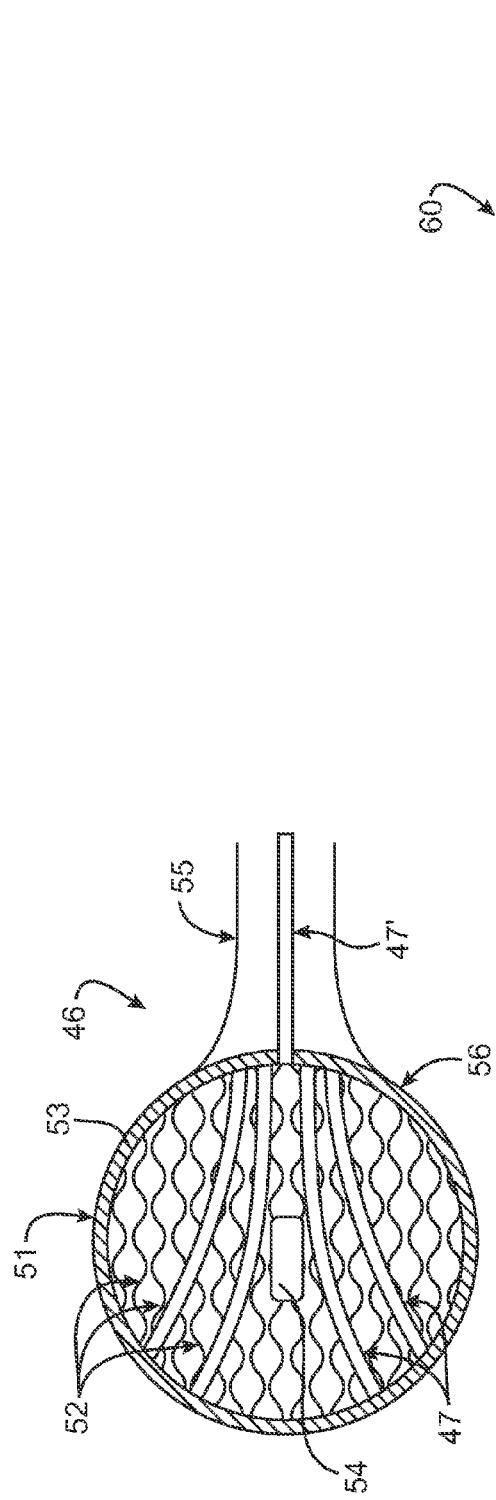
Figure 12:
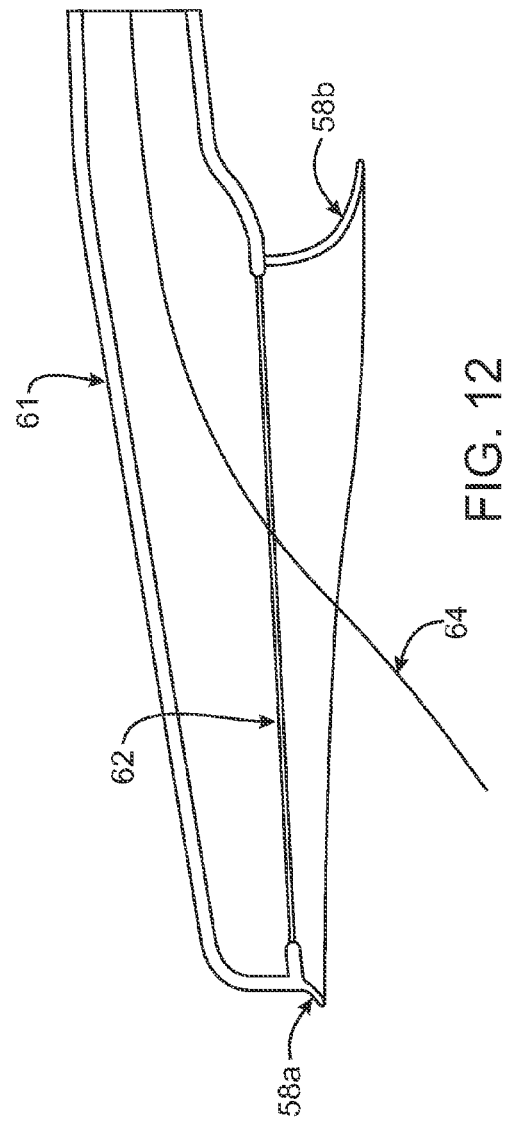
Figure 12A:
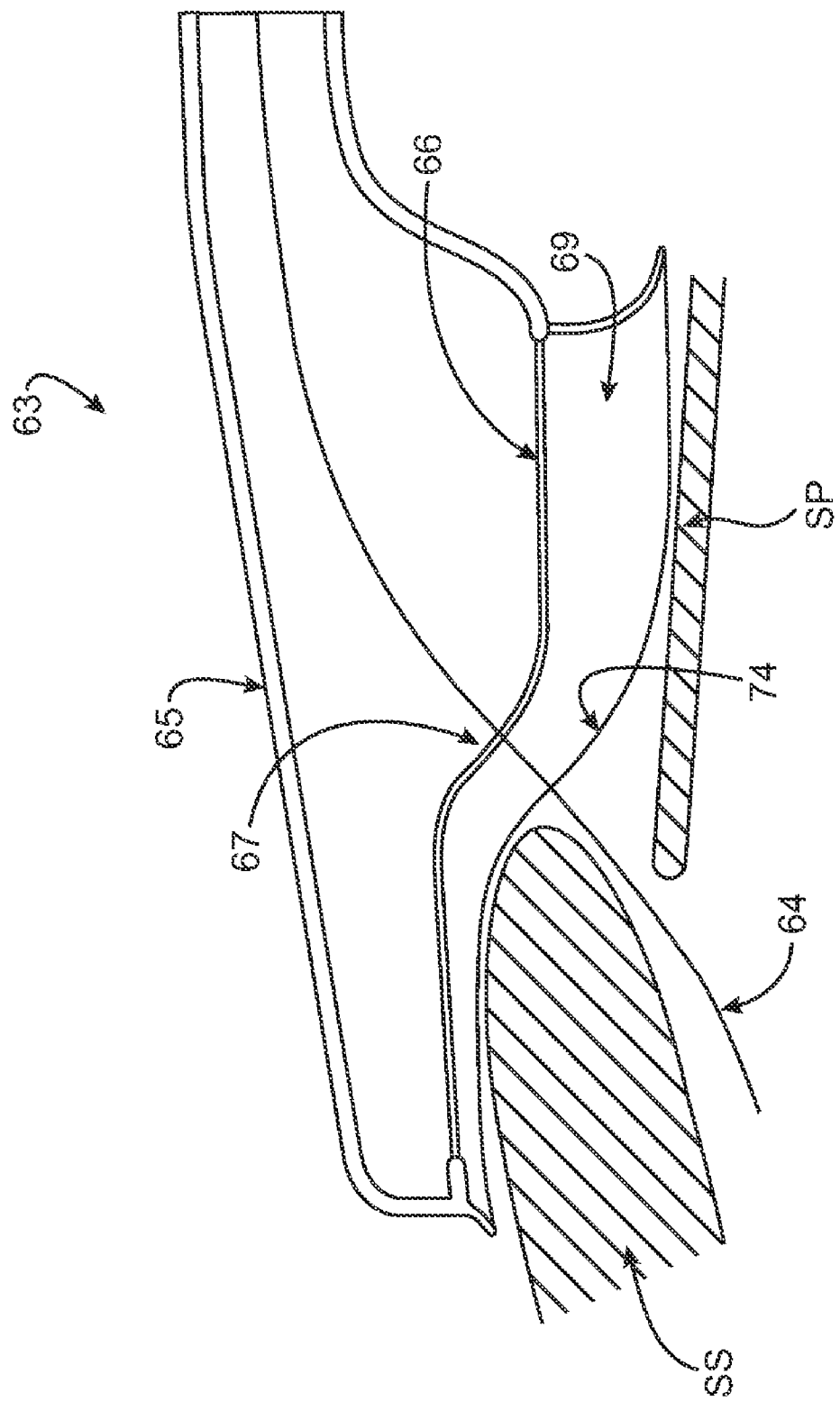
Figure 15:
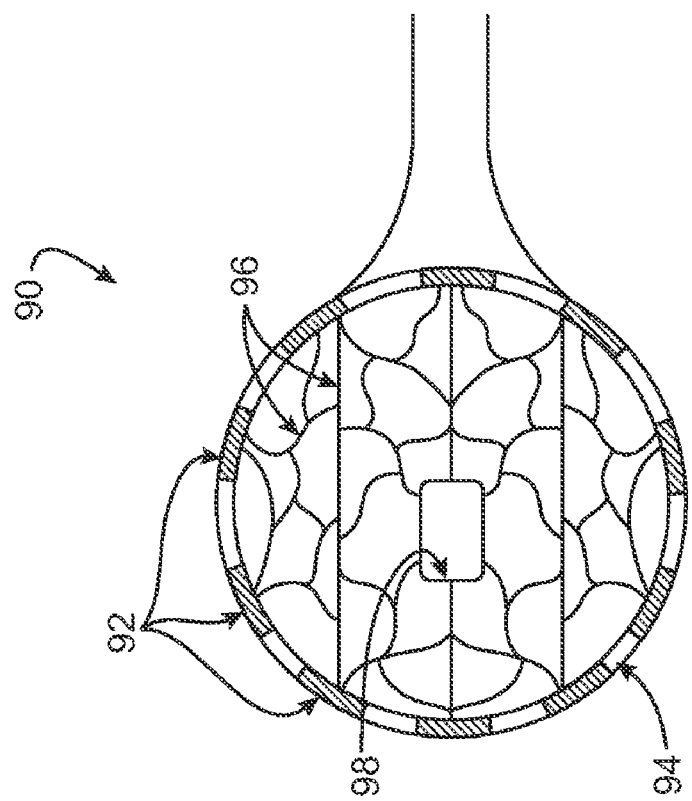
Figure 14:
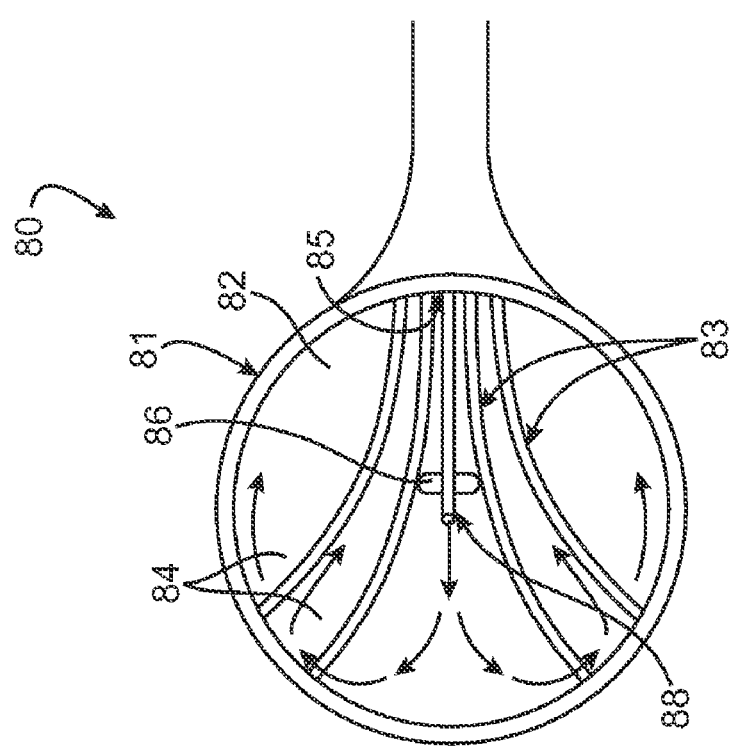
Figure 15A:
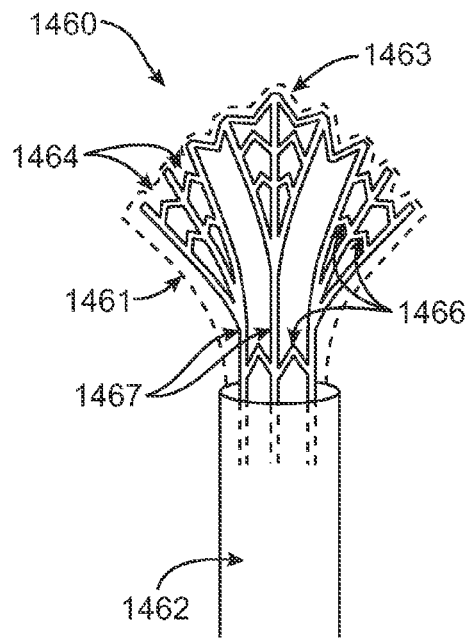
Figure 15B:
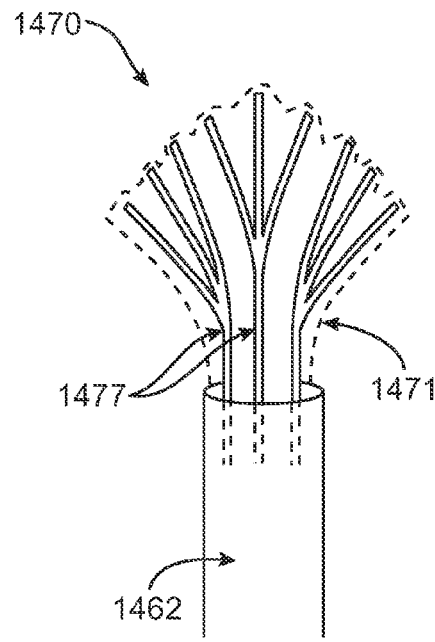
Figure 15C:
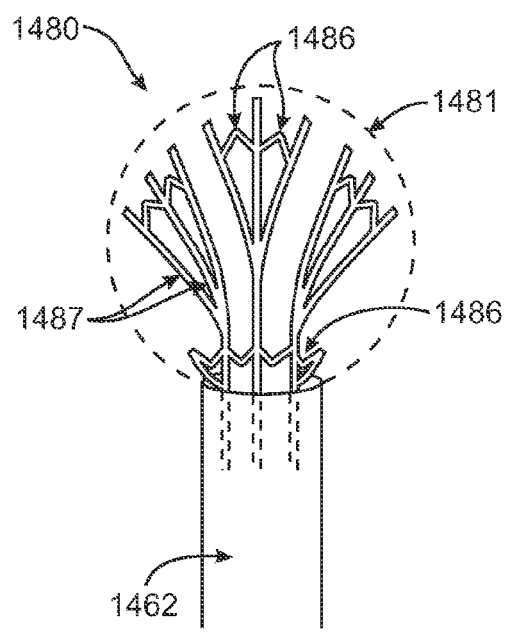
Figures 15D, 15E:
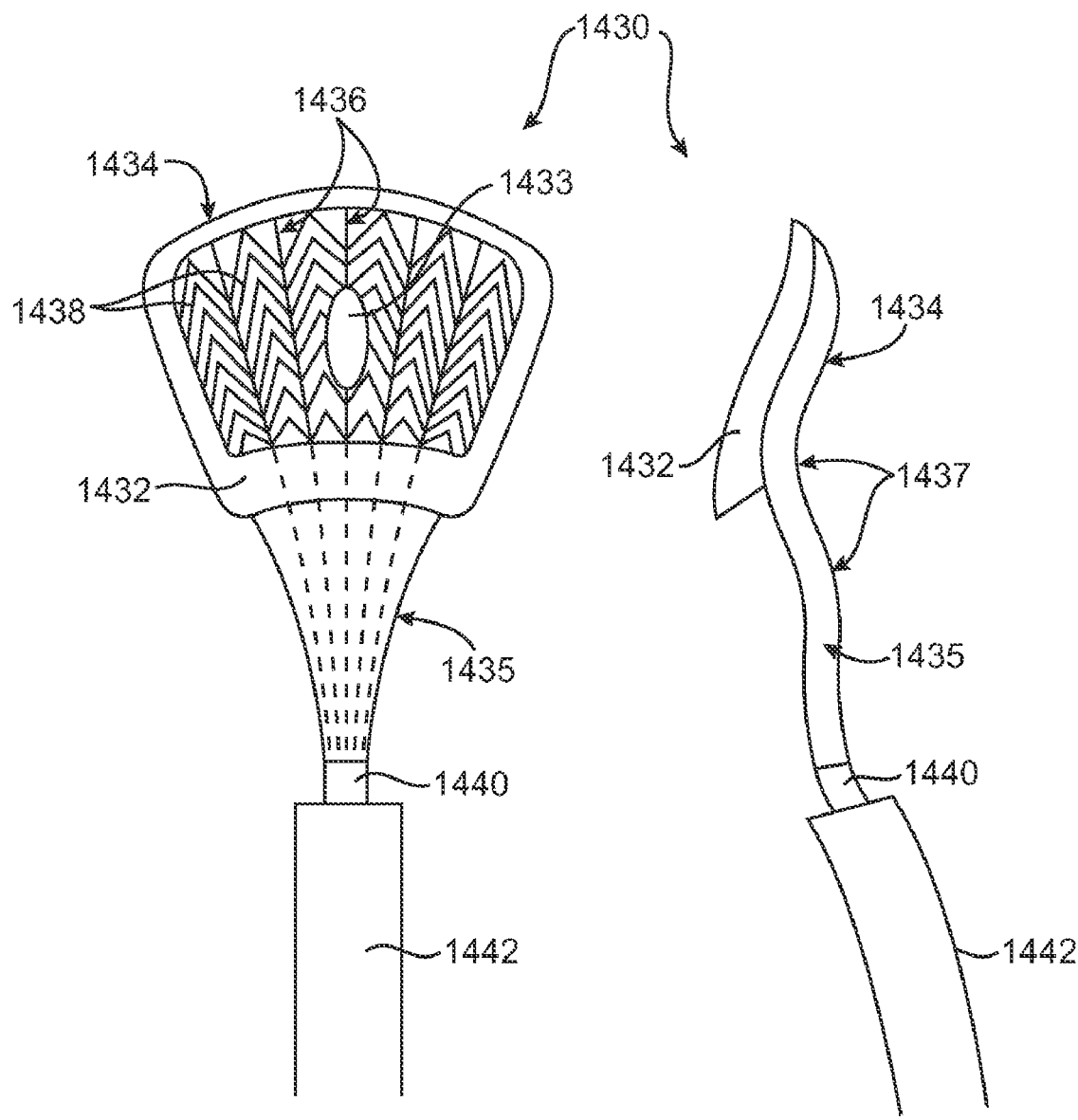
Figure 18:
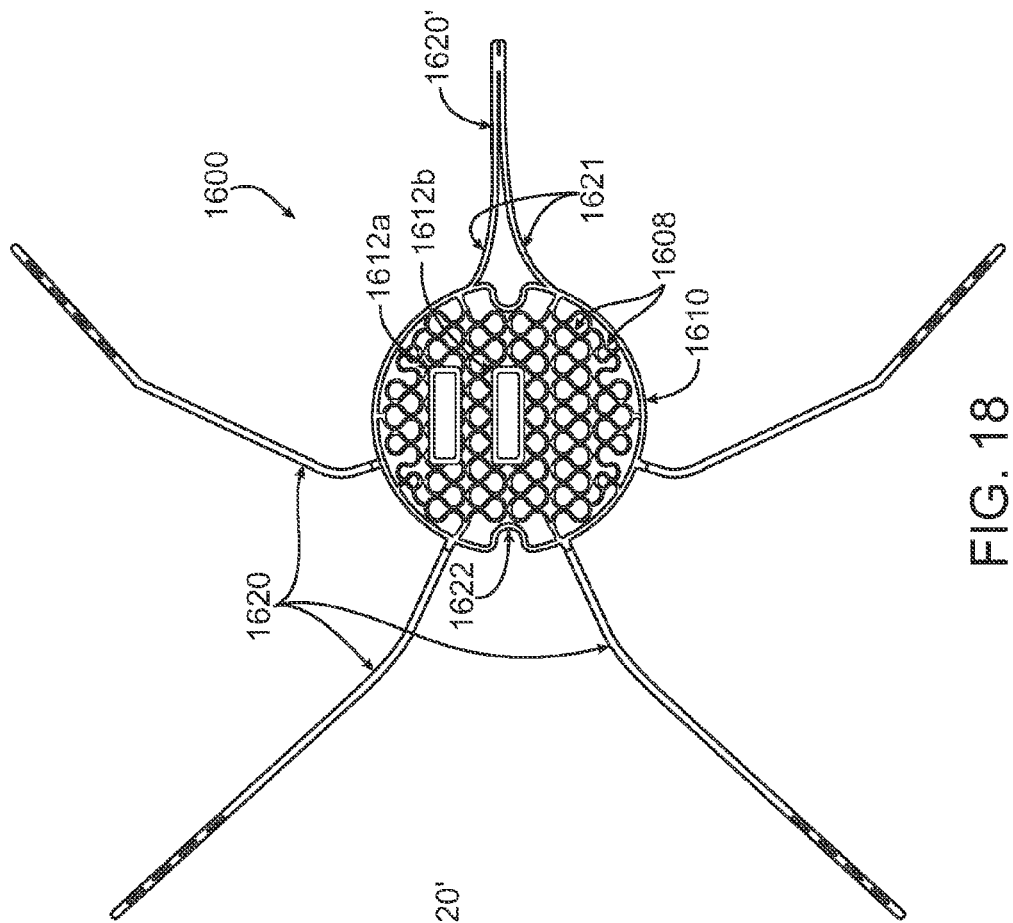
Figure 17:
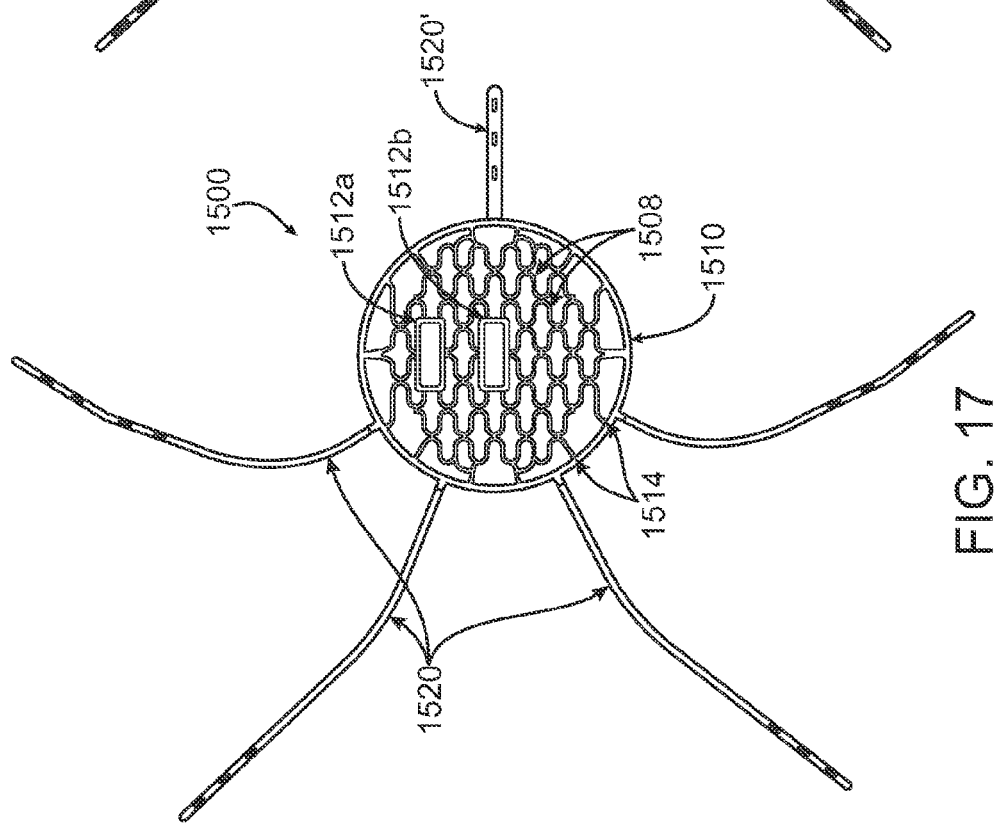
Figure 19:
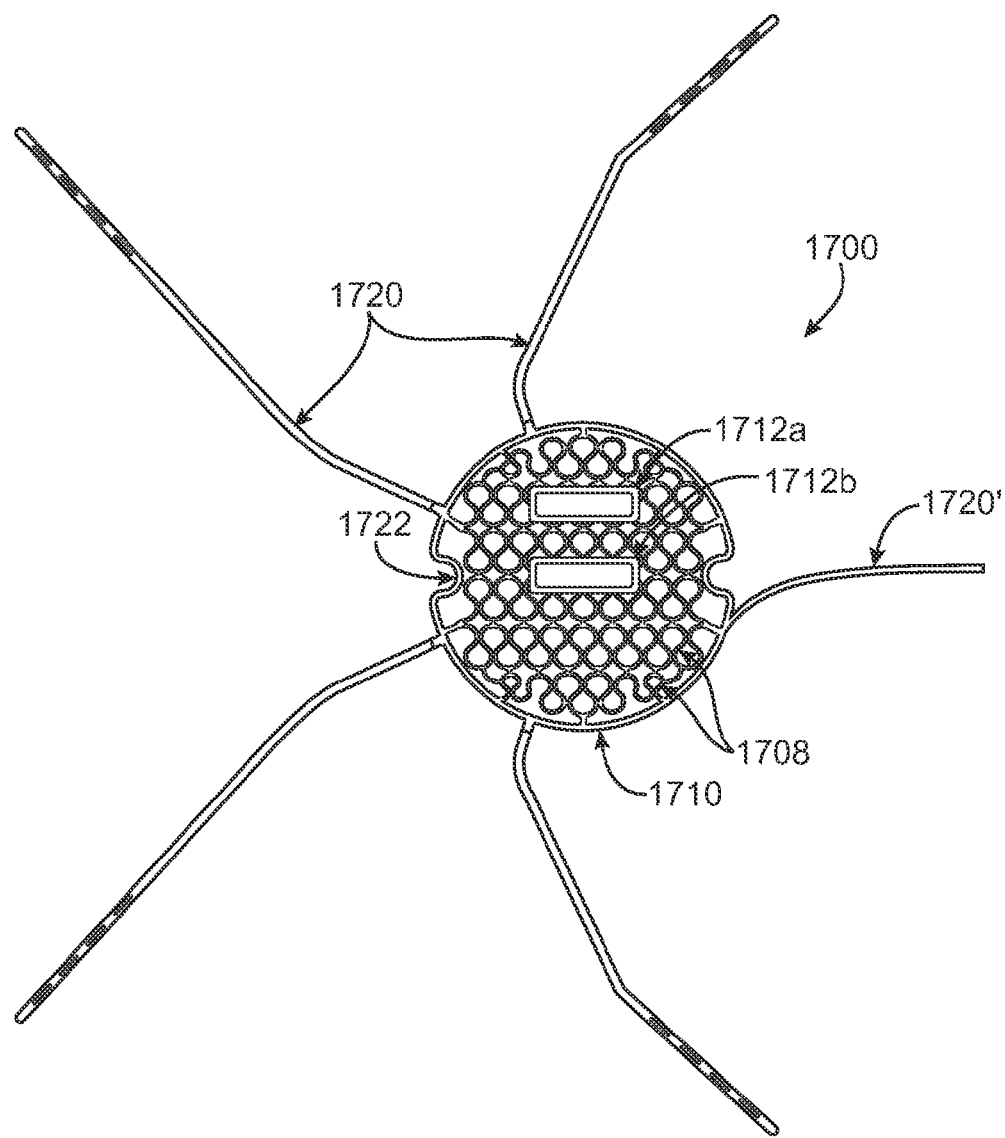
Figure 20:
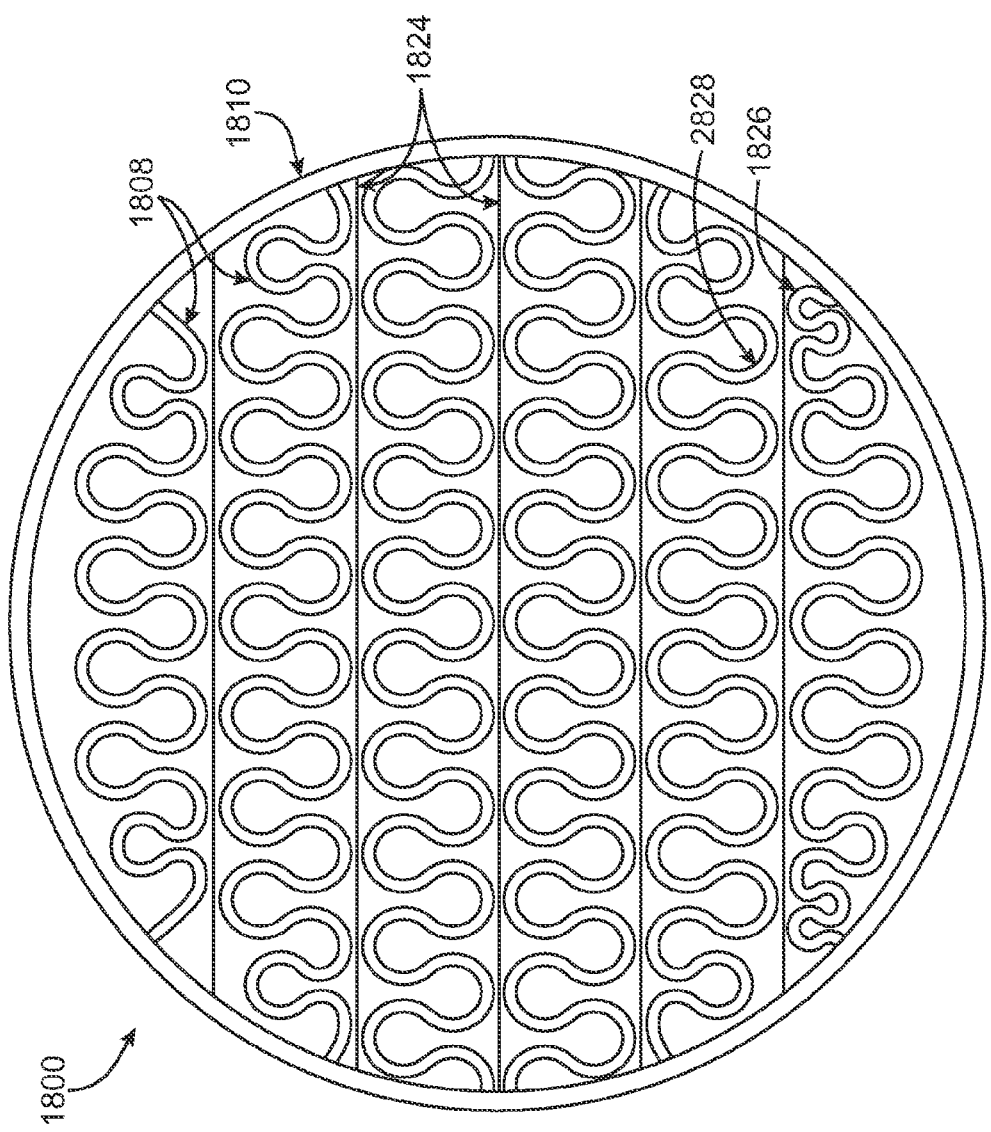
Figure 21:
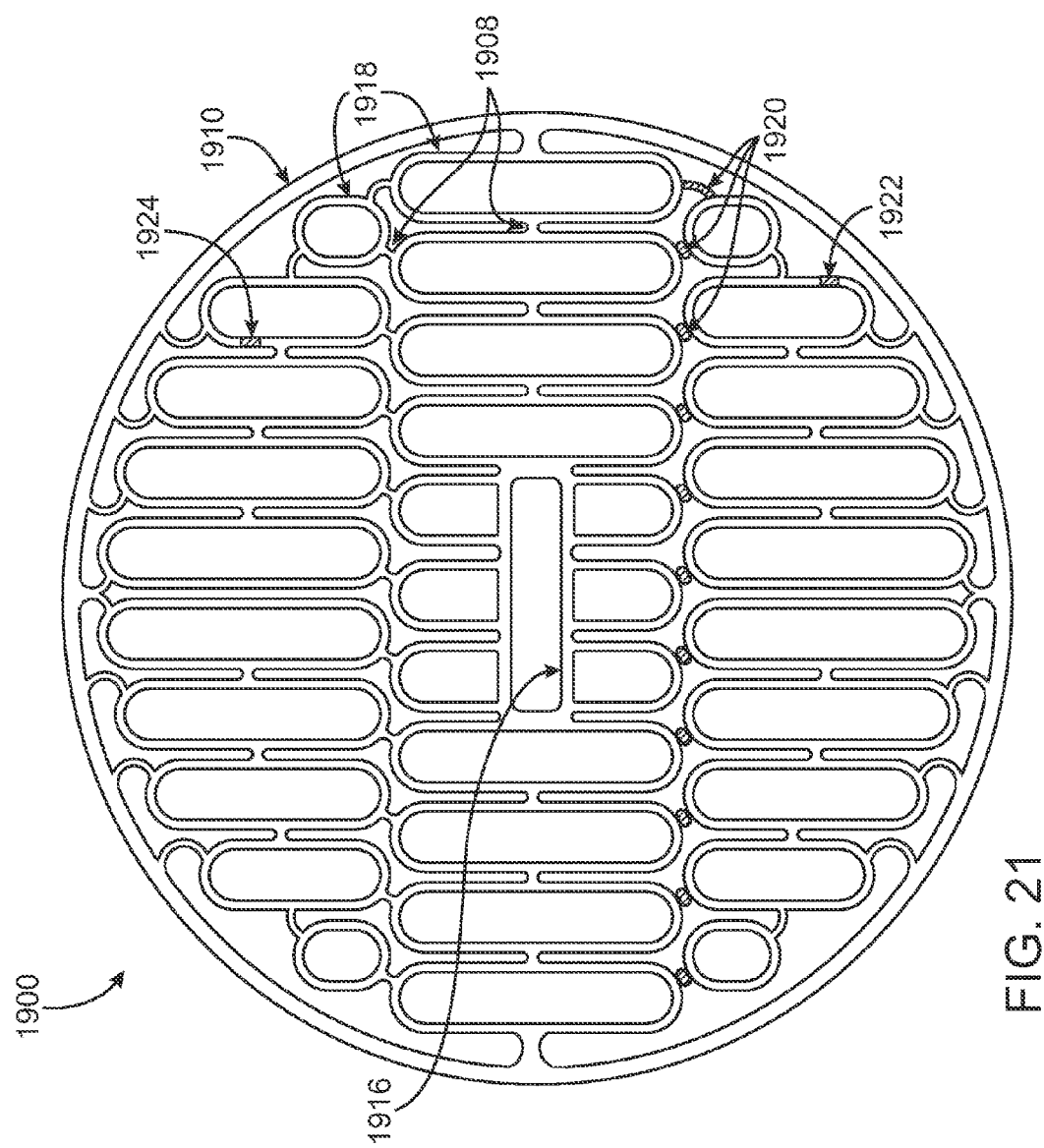
Figure 22:
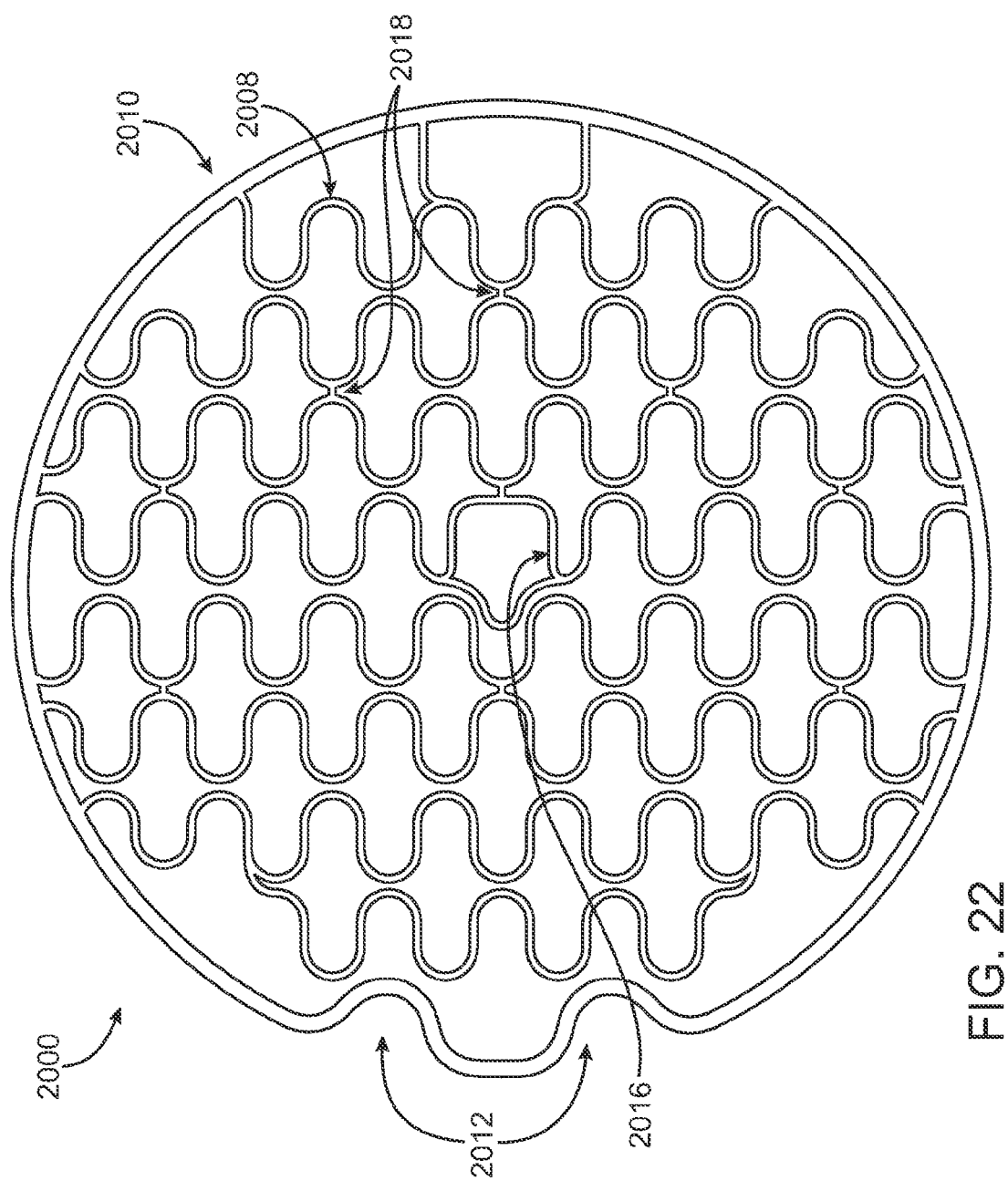
Figure 23:
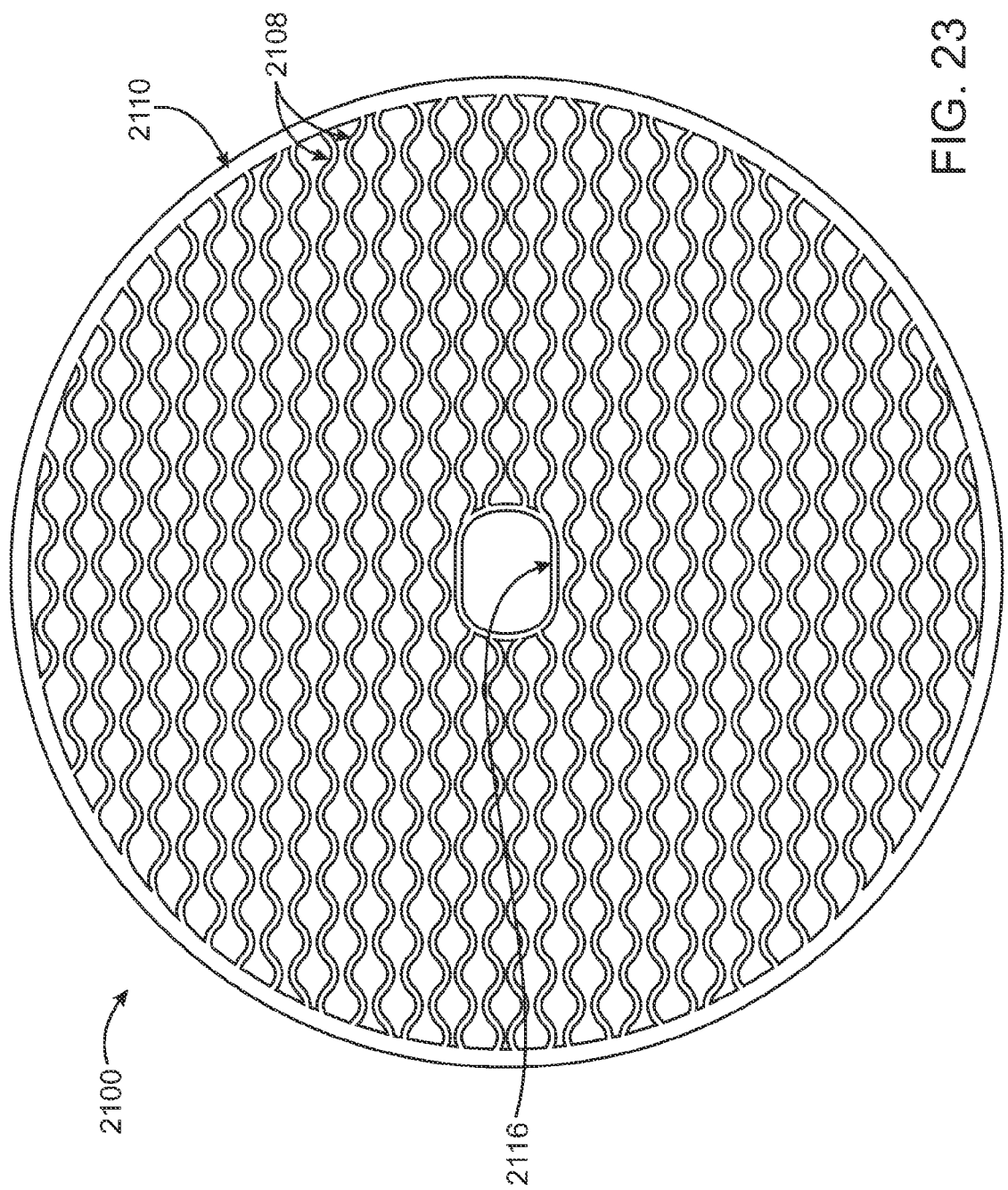

FIGS. 2G', 2G" and 2G"A are inferior, superior and end-on views, respectively, of an electrode housing of a catheter device according to one embodiment of the present invention;

FIG. 3 is a perspective view of a distal end of a catheter device for treating an anatomic tissue defect according to one embodiment of the present invention;

FIGS. 3A and 3B are cross-sectional views of the catheter device in FIG. 3;

FIG. 4 is a perspective view of a distal end of a catheter device for treating an anatomic tissue defect according to another embodiment of the present invention;

FIGS. 5A and 5B are perspective views of a distal end of a catheter device for treating an anatomic tissue defect according to another embodiment of the present invention;

FIG. 6 is a perspective view of a distal end of a catheter device for treating an anatomic tissue defect according to another embodiment of the present invention;

FIG. 7 is a perspective view of a distal end of a catheter device for treating an anatomic tissue defect according to another embodiment of the present invention;

FIGS. 8A-8E demonstrate a method for treating an anatomic tissue defect (exemplified by a PFO) using a catheter apparatus according to an embodiment of the present invention;

FIGS. 9A-9E demonstrate another method for treating a PFO using a catheter apparatus according to another embodiment of the present invention;

FIG. 10 is a perspective view of the distal-most end of a catheter device for treating an anatomic tissue defect according to one embodiment of the present invention;

FIG. 11 is an inferior view of the distal-most end of the catheter device in FIG. 10;

FIG. 12 is a cross-sectional side view of the distal-most end of a catheter device for treating an anatomic tissue defect according to one embodiment of the present invention;

FIG. 12A is a cross-sectional side view of the distal-most end of a catheter device for treating an anatomic tissue defect, including a stepped housing and electrode, according to another embodiment of the present invention;

FIG. 13 is a cross-sectional side view of the distal-most end a catheter device for treating an anatomic tissue defect, including a movable electrode according to another embodiment of the present invention;

FIG. 14 is an inferior view of a distal housing of a catheter device for treating an anatomic tissue defect, showing irrigation fluid circulation through the housing according to one embodiment of the present invention;

FIG. 15 is an inferior view of a distal housing of a catheter device for treating an anatomic tissue defect, showing an electrode with a discontinuous rim to enhance collapsibility according to one embodiment of the present invention;

FIG. 15A is an inferior view of a distal end of a catheter device for treating an anatomic tissue defect, having a fan-shaped, laterally collapsible electrode with a discontinuous rim and fan-shaped housing to enhance collapsibility according to one embodiment of the present invention;

FIG. 15B is an inferior view of a distal end of a catheter device for treating an anatomic tissue defect, having a fan-shaped, laterally collapsible electrode with no outer rim and a fan-shaped housing to enhance collapsibility according to one embodiment of the present invention;

FIG. 15C is an inferior view of a distal end of a catheter device for treating an anatomic tissue defect, having a fan-shaped, laterally collapsible electrode with no outer rim and a circular housing to enhance collapsibility according to one embodiment of the present invention;

FIGS. 15D and 15E are bottom and side views, respectively, of a distal portion of a catheter device for treating an anatomic tissue defect, including a fan-shaped housing to enhance collapsibility according to one embodiment of the present invention;

FIGS. 15F and 15G are side views of a distal portion of a catheter device for treating an anatomic tissue defect, having a sheath with a slanted distal end according to one embodiment of the present invention;

FIGS. 16A-16E are diagrammatic illustrations of a distal end of a catheter device, demonstrating a method for exposing and retracting a distal housing and electrode of the device according to one embodiment of the present invention;

FIG. 17 is a top view of an electrode with attachment members for use in a catheter device for treating an anatomic tissue defect according to one embodiment of the present invention;

FIG. 18 is a top view of an electrode with attachment members for use in a catheter device for treating an anatomic tissue defect according to another embodiment of the present invention;

FIG. 19 is a top view of an electrode with attachment members for use in a catheter device for treating an anatomic tissue defect according to another embodiment of the present invention;

FIG. 20 is an electrode pattern for use in a catheter device for treating an anatomic tissue defect according to one embodiment of the present invention;

FIG. 21 is an electrode pattern for use in a catheter device for treating an anatomic tissue defect according to another embodiment of the present invention;

FIG. 21A is a layered PCB electrode with encapsulated, disconnected electrode surfaces, according to one embodiment of the present invention;

FIG. 21B is a cross-section of a layered PCB electrode with encapsulated, disconnected electrode surfaces, according to one embodiment of the present invention;

FIG. 22 is an electrode pattern for use in a catheter device for treating an anatomic tissue defect according to another embodiment of the present invention; and FIG. 23 is an electrode pattern for use in a catheter device for treating an anatomic tissue defect according to another embodiment of the present invention.

FIGS. 24A-24C are electrode patterns according to various alternative embodiments of the present invention.

DETAILED DESCRIPTION OF THE INVENTION

Devices and methods of the present invention generally provide for treatment of anatomic defects in human tissue, such as patent foramen ovale (PFO), atrial septal defect, ventricular septal defect, left atrial appendage (LAA), patent ductus arteriosis, vessel wall defects and/or the like through application of energy. In addition, electrophysiological defects, such as atrial fibrillation, supraventricular tachacardia (SVT), atrial flutter, A-V node re-entry, and Wolf Parkinson White syndrome, may be treated using various embodiments of the present invention. Therefore, although the following descriptions and the referenced drawing figures focus primarily on treatment of PFO, any other suitable tissue defects, such as but not limited to those just listed, may be treated in various embodiments.

Figure 1:
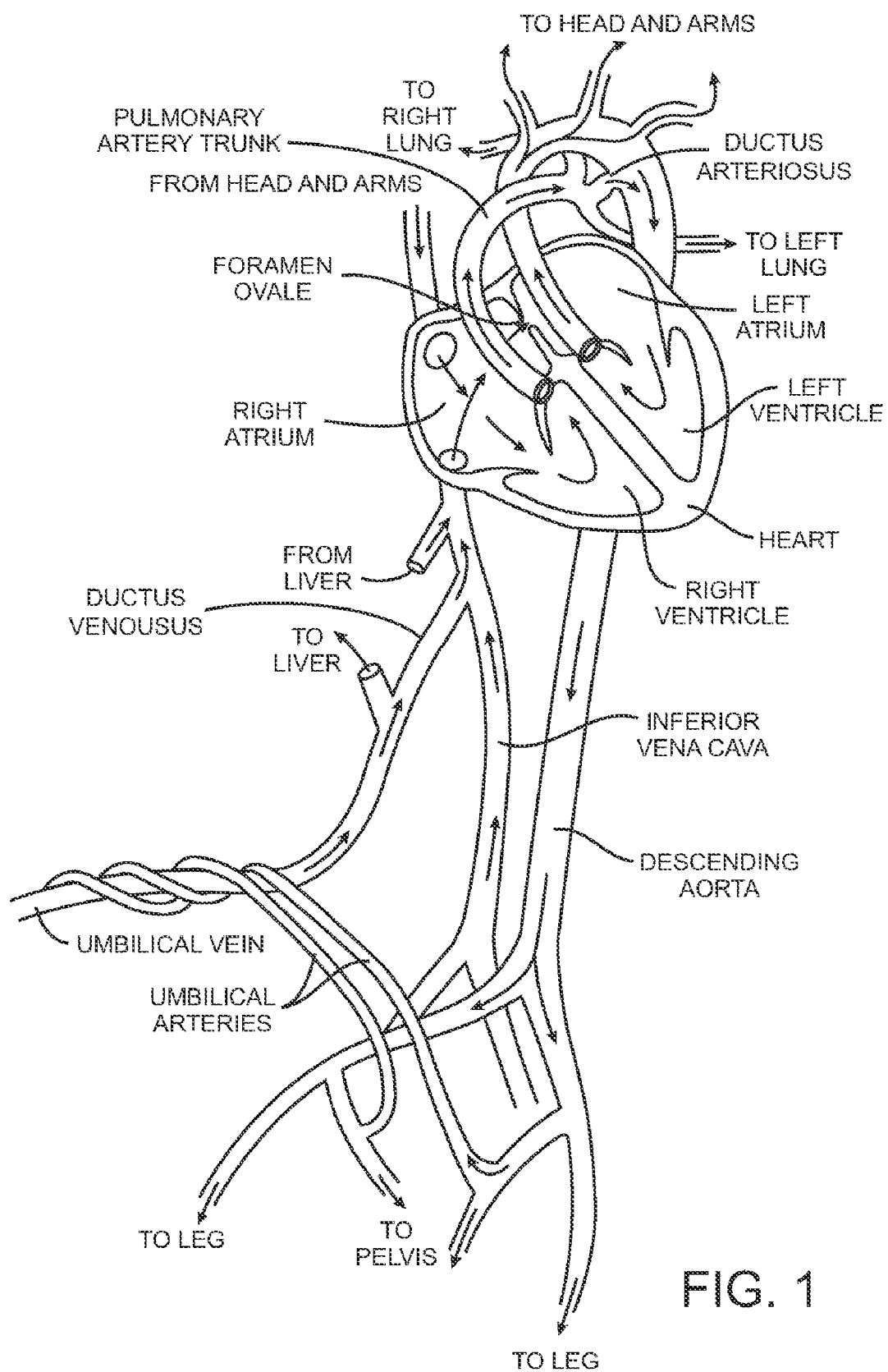
FIG. 1 is a diagram of the fetal circulation.

As mentioned in the background section above, FIG. 1 is a diagram of the fetal circulation. The foramen ovale is shown, with an arrow demonstrating that blood passes from the right atrium to the left atrium in the fetus. After birth, if the foramen ovale fails to close (thus becoming a PFO), blood may travel from the right atrium to the left atrium or vice versa, causing increased risk of stroke, migraine and possibly other adverse health conditions, as discussed above.

I. Catheter Device

Figure 1A:
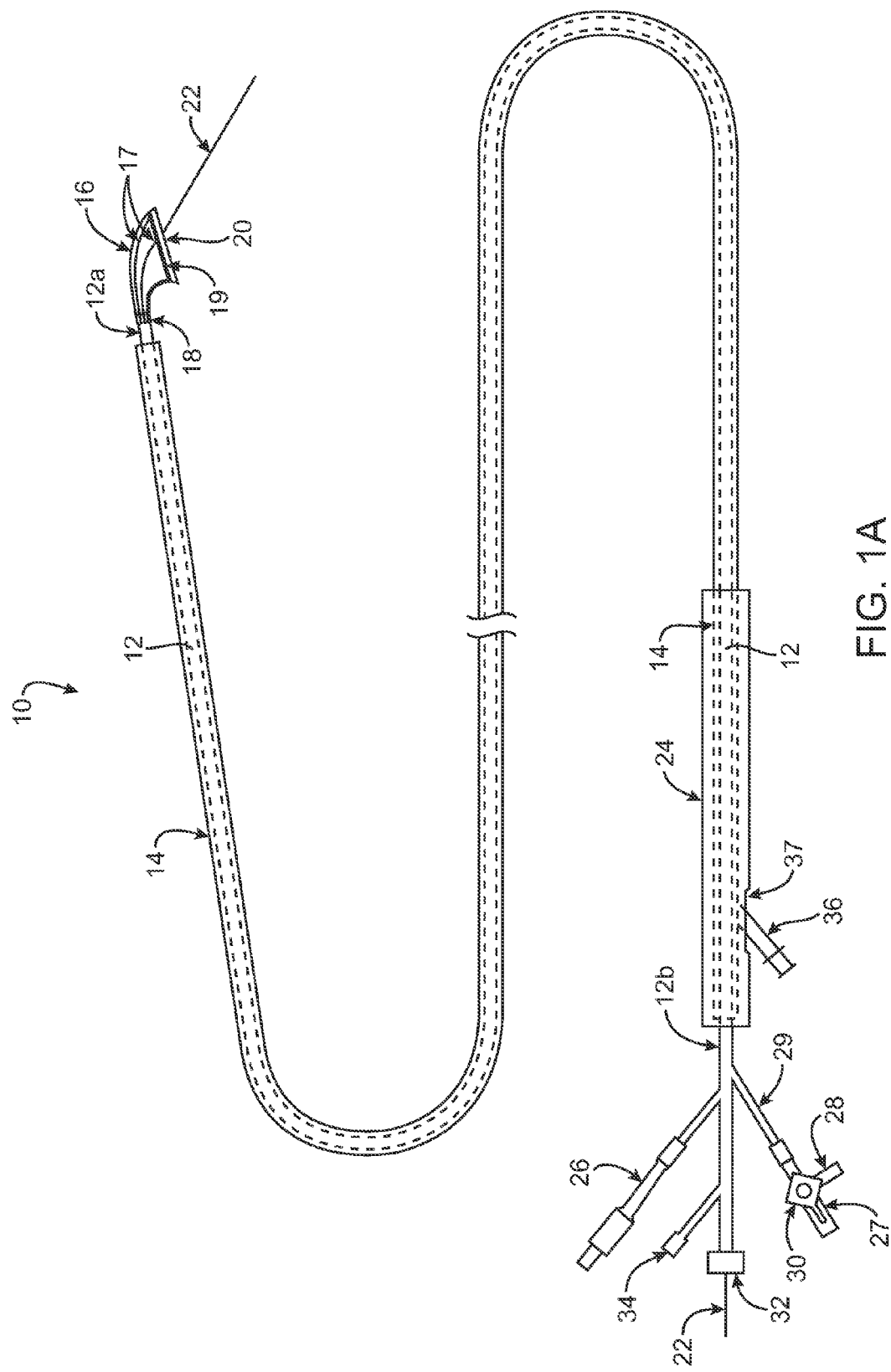
FIG. 1A is a perspective view of a catheter device for treating an anatomic tissue defect according to one embodiment of the present invention.

Referring now to FIG. 1A, in one embodiment a catheter device 10 for treating an anatomic tissue defect according to one embodiment includes an elongate catheter shaft 12 having a proximal end 12b and a distal end 12a, a sheath 14 (or "sleeve") disposed over at least part of shaft 12, a handle 24 coupled with a proximal end of sheath 14, and a collapsible housing 16 coupled with catheter shaft distal end 12a. Coupled with housing 16 are a distal flexible foot 20 for contacting tissue, an electrode 19 (or other suitable energy transmission member in alternative embodiments) for transmitting radiofrequency (RF) energy to tissues, attachment members 17 (or "struts") for coupling electrode 19 with housing 16 and for providing support to housing 16, and a radiopaque marker 18 for coupling attachment members 17 with housing 16 and/or catheter body distal end 12a and for facilitating visualization of device 10. A guidewire 22 is passed through catheter 10 from the proximal end through the distal end. In the embodiment shown, catheter body proximal end 12b includes an electrical coupling arm 26, a guidewire port 32 in communication with a guidewire lumen (not shown), a fluid infusion arm 34 in fluid communication with the guidewire lumen, and a suction arm 29 including a suction port 27, a fluid drip port 28, a valve switch 30 for turning suction on and off. Fluid drip port 28 allows fluid to be passed into a suction lumen to clear the lumen, while the suction is turned off. A flush port 36 is coupled with sheath 14 and extends through an opening 37 in handle 24. Flush port 36 allows fluid to be introduced between sheath 14 and catheter body 12, to flush that area, and its connection to sheath 14 and passage through opening 37 prevents rotation of sheath 14 relative to catheter body 12.

Many of the above-mentioned features are described in further detail below. In alternative embodiments, additional features or fewer features may be included on catheter device 10. For example, a number of modifications may be made to catheter body proximal end 12b without departing from the scope of the invention. Therefore, the following description of embodiments is intended to be primarily exemplary in nature and should not be interpreted to limit the scope of the invention as it is described in the claims.

Figure 2:
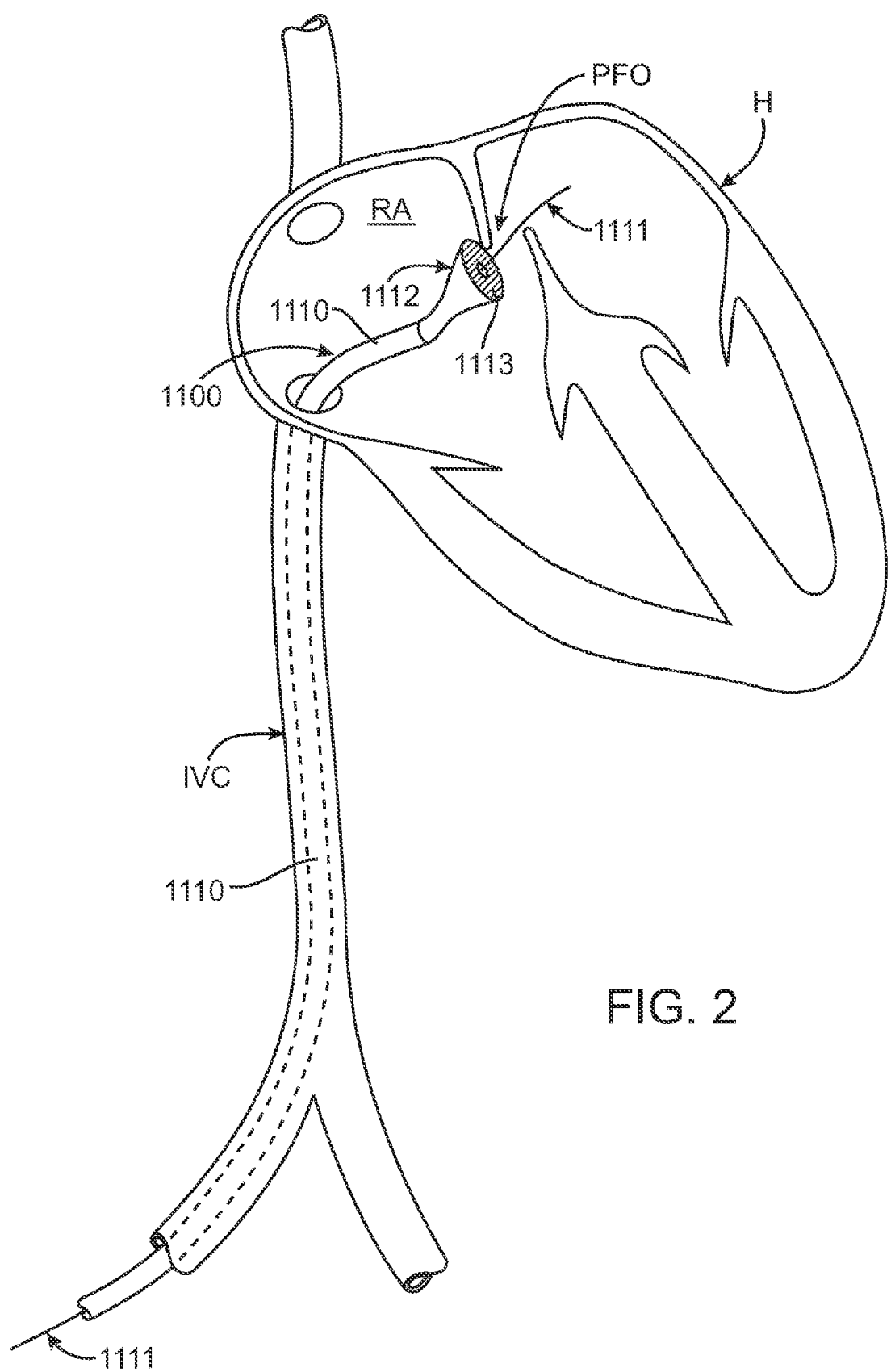
FIG. 2 is a diagram of a catheter device for treating an anatomic tissue defect (exemplified as a PFO), according to one embodiment of the present invention, the catheter passing through the inferior vena cava and into the right atrium, with a guidewire extending through the defect.

That being said, and with reference now to FIG. 2, a distal portion of one embodiment of a catheter device 1100 for treating an anatomic tissue defect is shown within a cross-section of a heart H, in position to treat a PFO. In one embodiment, catheter device 1100 may be advanced through the inferior vena cava IVC into the right atrium RA of the heart H. Catheter device 1100 generally includes a sheath 1110, a collapsible housing 1112 extending from the distal end of sheath 1110, and an electrode 1113 (or one or more other energy transmission members, in alternative embodiments) coupled with housing 1112. Catheter device 1100 may be advanced over a guidewire 1111 extending through a PFO or other tissue defect. Electrode 1113 comprises a planar, metallic electrode disposed within or near the distal end of housing 1112, as will be described in further detail below in reference to FIGS. 2C through 2G. Housing 1112 acts as a vacuum application member to contact and apply vacuum to tissues to bring them together. For example, vacuum may be applied via housing 1112 to septum primum and septum secundum tissues of the PFO to bring those tissues together. RF energy is then transmitted to the tissues via electrode 1113 to close the PFO, as will be described further below.

Figure 2A:
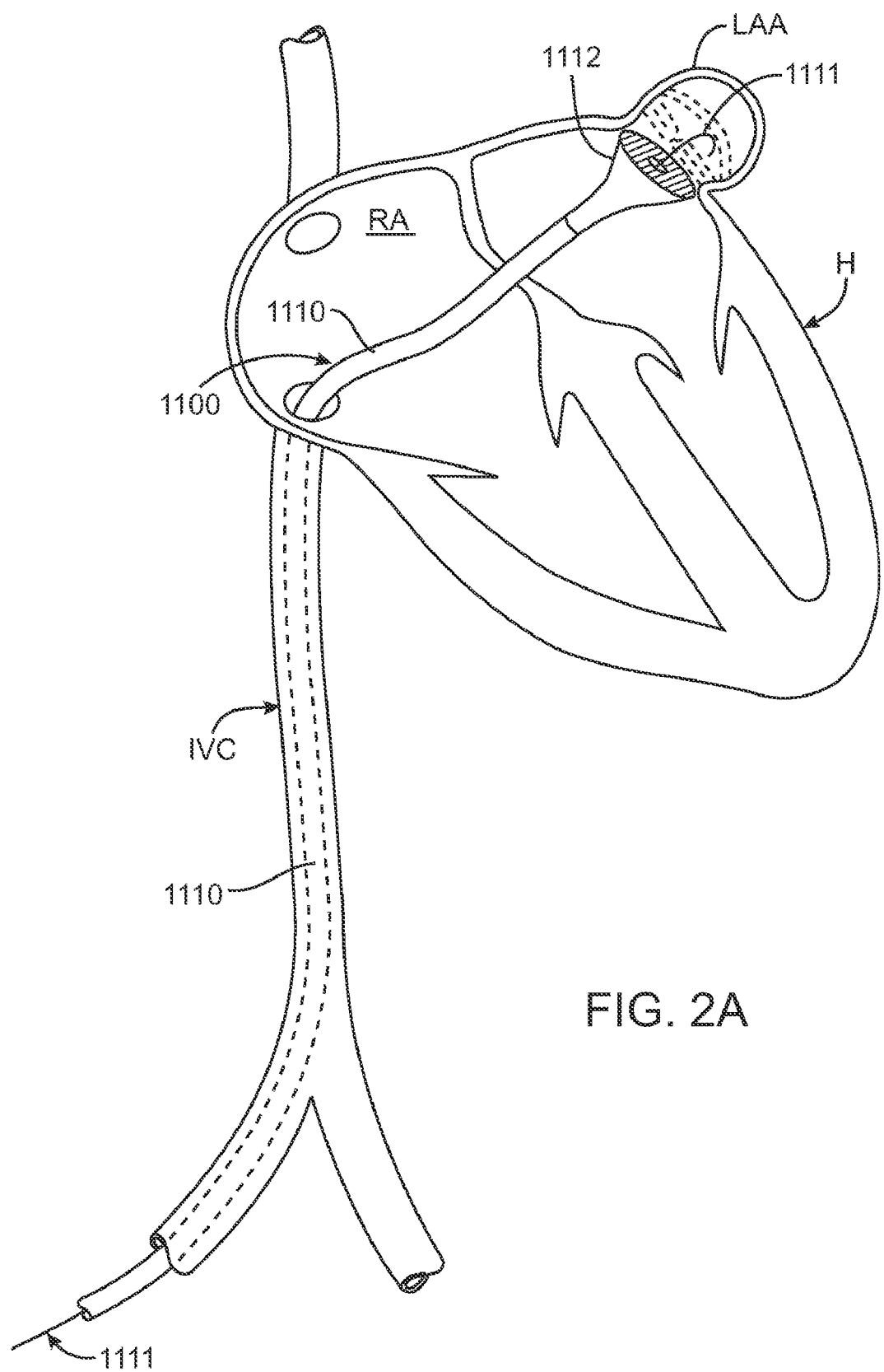
FIG. 2A is a diagram of a catheter device for treating an anatomic tissue defect (exemplified as a left atrial appendage (LAA)), according to one embodiment of the present invention, the catheter passing through the inferior vena cava, across the interatrial septum, and into the left atrium to the mouth of the LAA.

FIG. 2A shows catheter device 1100 from FIG. 2, advanced over a guidewire 1111 and to the mouth of a left atrial appendage (LAA) defect. Vacuum is applied via housing 1112 to approximate the tissue at the mouth of the LAA, seal or flatten the defect (shown in dotted lines), and trap any clot residing in the defect, to prevent it from embolizing. The vacuum may cause the mouth of the LAA to close, or it may cause the LAA to empty and lay flat, approximating one edge of the mouth to the tissue on the opposite inner wall of the LAA (also shown in dotted lines), or it may approximate tissue in some other geometry.

Figure 2B:
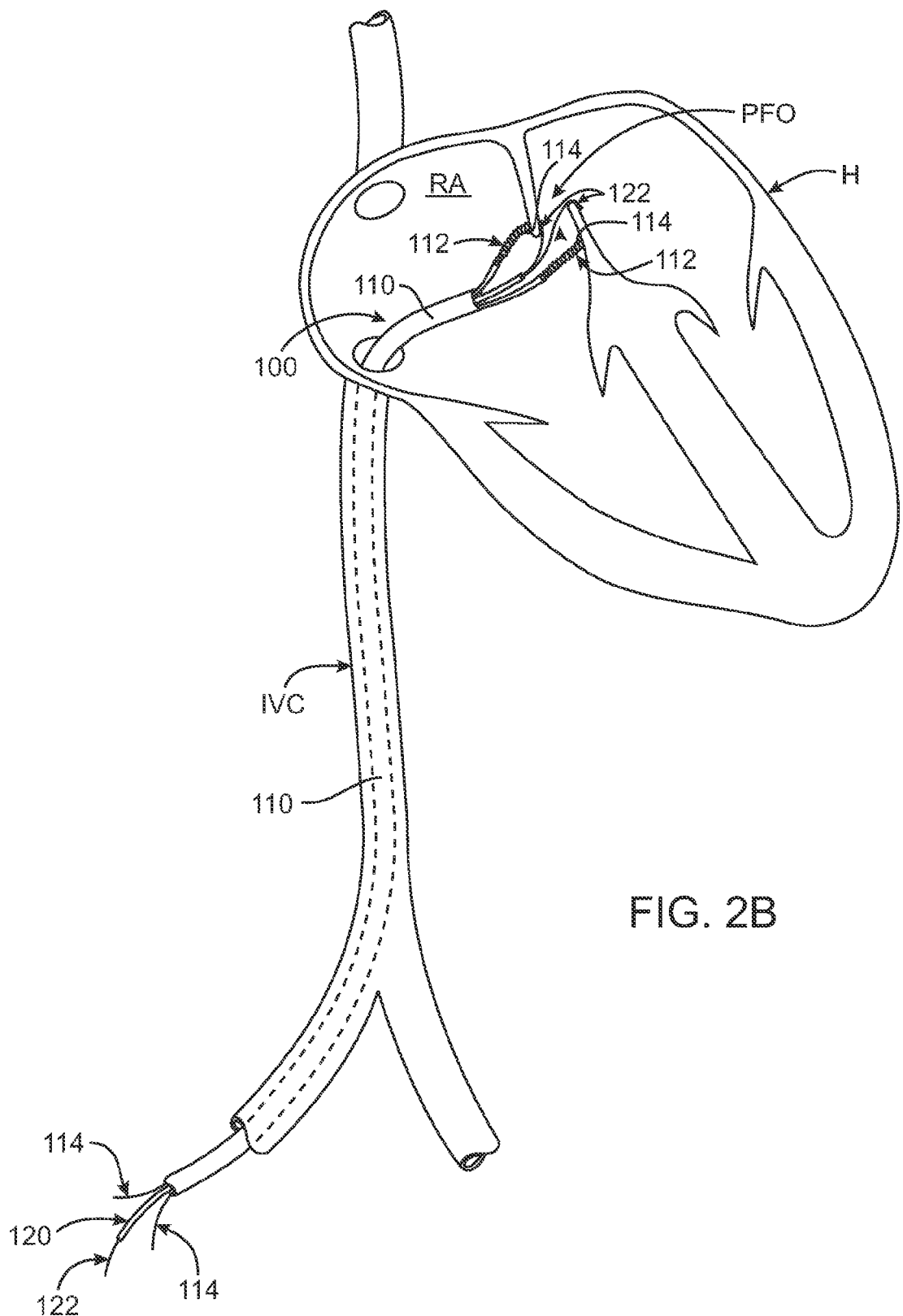
FIG. 2B is a diagram of a catheter device for treating an anatomic tissue defect (exemplified as a PFO), according to another embodiment of the present invention, the catheter passing through the inferior vena cava and into the right atrium, with a guidewire extending through the defect.

FIG. 2B depicts an alternative embodiment of a catheter device 100 for treating an anatomical tissue defect. In this embodiment, catheter device 100 includes an elongate sheath 110, one or more tissue apposition members 112 extendable out of the distal end of sheath 110, and one or more energy transmission members 114 coupled with tissue apposition members 112. Catheter device 110 may be slidably disposed over a guide member 120, such as a guide catheter, a guidewire, or the like. Guide member 120 may include, for example, an inner guidewire 122 with an expanding or split distal end or other similar features for deploying within the PFO to help appose the adjacent tissues. In some embodiments, as described further below, the split and/or expandable distal end of guidewire 122 may comprise (or be coupled with) one or more energy transmission members 114. As discussed above and described further below, catheter device 100 is generally used to bring together tissues surrounding and/or adjacent the PFO or other anatomical tissue defect and transmit energy to the tissues to close or treat the defect.

Figure 2C:
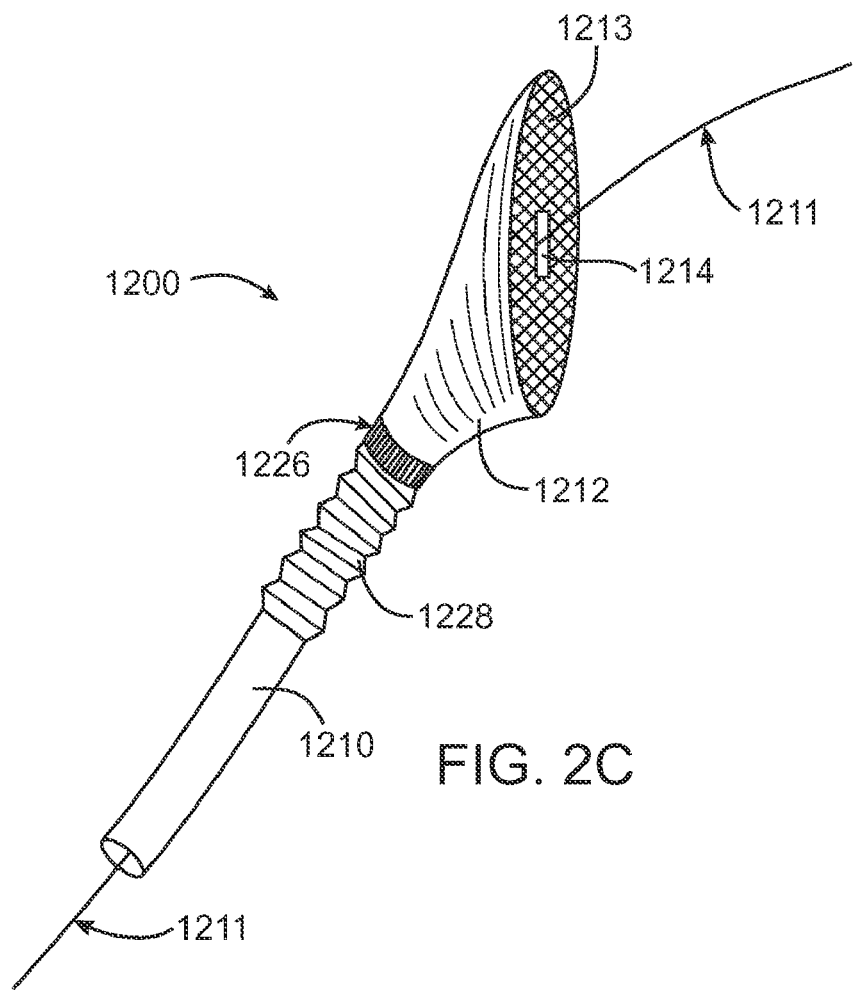
FIG. 2C is a perspective view of a distal end of a catheter device for treating an anatomic tissue defect according to one embodiment of the present invention.
Figure 2D:
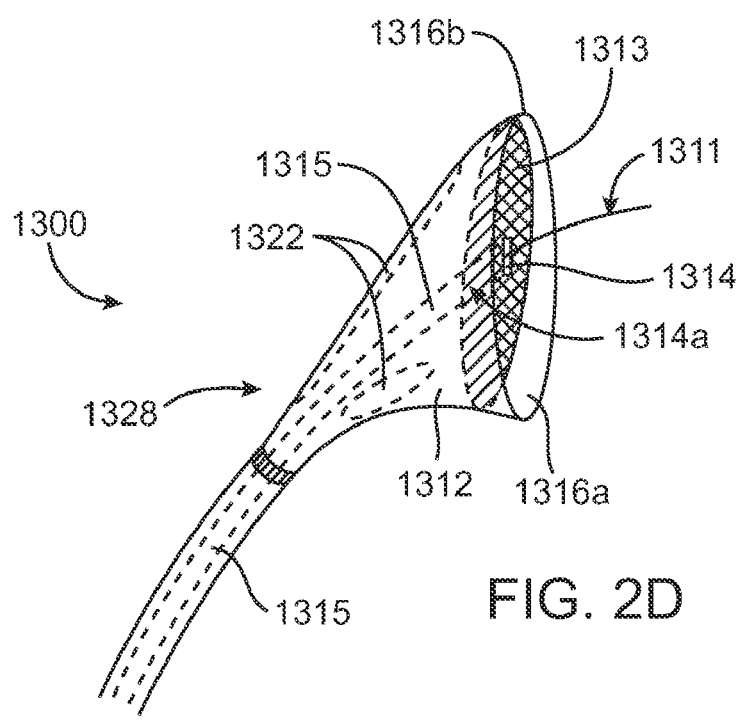
FIG. 2D is a perspective view of a distal end of a catheter device for treating an anatomic tissue defect according to another embodiment of the present invention.

Referring now to FIGS. 2C and 2D, distal portions of two embodiments of tissue treatment devices 1200, 1300 are shown. In FIG. 2C, treatment device 1200 includes a catheter body, having a flexible neck 1228 to allow for deflection and/or active steering, and a radiopaque marker 1226. FIG. 2D depicts a neck 1328 that has a preformed bend. At the distal end of catheter body 1210 is attached a vacuum application member or housing 1212. At the distal end of housing 1212, a planar electrode 1213 for transmitting RF energy is disposed. The embodiment shown in FIG. 2D demonstrates several additional optional features of a tissue treatment device 1300, and in particular a tissue apposition member. In such an embodiment, a tissue apposition member may include a vacuum application housing 1312, for example, may include multiple ribs 1322 or ridges, grooves or the like, to provide support to vacuum housing, thus preventing its collapse when vacuum is applied. Vacuum housing 1312 itself may be made of any suitable material or combination of materials, such as but not limited to any suitable polymers. Ribs 1322 may be made of the same or different material as the rest of housing 1312, and are generally thickened or heightened portions of material. Additionally or alternatively, multiple struts 1317 (FIG. 2F) may be embedded within or attached to the wall of housing 1312 for providing similar support. Struts 1317 may also be separate from the housing and attached to the catheter shaft and electrode to allow for torque of the electrode itself. Alternatively, guidewire lumen 1315 as detailed below may serve a similar function, eliminating the need for strut elements. Grooves or valleys on the inner surface of housing 1312 between ribs 1322 may also enhance flow of substances, such as blood or infused fluid.

Referring to FIGS. 2D-2F, another optional feature of tissue apposition member of tissue treatment device 1300 includes a flexible foot 1316 at the distal end of vacuum housing 1312. In various embodiments, flexible foot 1316 may comprise simply an extension of the material of housing 1312, or in other embodiments it may comprise a different material. In some embodiments, foot 1316 is formed by recessing electrode 1313 within vacuum housing 1312. In one embodiment, foot 1316 comprises an asymmetric cylinder including a taller side 1316*a* and a shorter side 1316*b*. Such an asymmetric foot 1316 may facilitate creation of a seal between foot 1316 and tissues that are being brought together. Generally, foot 1316 is made of a flexible polymer such as those set forth above in this specification, or other material so as to promote engagement of foot 1316 with tissues while preventing unwanted tissue damage. Foot 1316 is also adapted to not roll in on itself when engaged with tissue, but to be conformable to the tissue to accommodate and seal over the geometry of the tissue defect which may include varying tissue depth or elevations, oddly shaped or sized perimeter, or multiple defects (such as in multiple flaps found in PFOs, or inhomogeneous tissue (e.g. thin and thicker). Foot 1316 may be formed of a material such as silicone that can be molded such that the periphery of the foot cylinder may be thinner than the main body. Given the variability of certain defects and the desirability of having a catheter design that accommodates varying tissue geometry, it may be desirable to design the foot 1316 to expand or contract distance D as shown in FIG. 2F.

FIG. 2E further depicts the catheter 1300 and housing 1312. Catheter shaft 1310 may be formed of a braided construction to allow for kink resistance, pushability and torqueability of catheter shaft 1310 to the desired placement. To further facilitate placement and positioning of catheter shaft 1310, it may sometimes be desirable to torque the catheter from side to side and/or to advance the device over more than one guidewire. FIG. 2G' shows such an embodiment of a housing 1312 having multiple, asymmetric guidewire apertures 1314. Further, neck portion 1328 (FIG. 2E) may be preformed to have a radius of curvature ($\theta$ between a range of 0 to 90 degrees) to facilitate positioning of catheter 1300 over a tissue defect.

One or more structural elements, such as a struts 1317, a resilient mesh embedded in the housing and/or a torque cable or rod attached to the electrode may be incorporated to allow the electrode and housing 1312 to be torqued and maneuvered. One such housing 1312 is further detailed in FIGS. 2F-2G", showing struts 1317 optionally embedded into housing material to provide control and rigidity to housing 1312 when shaft 1310 is torqued. Struts may extend the length of the catheter, or be terminated at the point of the radiopaque marker (RO) on the catheter shaft. In addition, struts may be truncated to only run a partial length of the housing as shown in FIG. 2G" 1350. In a further embodiment, strut may be a single element that is rigidly coupled to the electrode to assist in lowering the profile of the housing while still allowing torque of the electrode. In some embodiments it may be advantageous to fabricate the struts and the electrode as a one piece construction. Struts may further incorporate radiopaque markings 1340 to assist in visual orientation of the catheter under fluoroscopy, ultrasound, or other imaging modalities. Such markings 1340 as shown in FIG. 2G" may include an asymmetric component 1341 on the housing to assist the user in differentiating the right side from the left side of the catheter housing. Markings may be formed from techniques known in the art such as plating, use of metal markers such as tantalum, platinum, stainless steel, or imbuing contrast agents into the catheter material such as barium sulfate and the like. In some embodiments, the electrode and housing 1312 may be retracted into catheter sheath 1351 for introduction and removal of the device in a percutaneous manner. For example, in one embodiment a housing measuring about 0.50 inch in diameter may be retracted into or deployed from a shaft opening having a diameter of about 0.10 inch. In another embodiment for treating larger defects, the housing may measure about 1.0 inch and be capable of collapsing into a catheter shaft with a diameter of about 0.18 inch.

Referring now to FIG. 3, another distal portion of an embodiment of a treatment apparatus 200 for treating an anatomical tissue defect is shown. Apparatus 200 includes a catheter device 210 coupled with a tissue apposition member 212 at its distal end. One or more energy transmission members 214 may be disposed through or within catheter device 210 and/or coupled with tissue apposition member 212. In some embodiments, catheter device 210 is slidably disposed over a guide catheter 220. Guide catheter 220 may contain one or more expandable elements 222, such as a guide wire or the like. One or more radiopaque markers 224, 226 may be included on catheter device 210, guide catheter 220 or both. Catheter device 210 may also include an isolation portion 228 for helping to stabilize tissue apposition member 212 during use, so that it is not caused to move due to the flexibility of catheter device 210.

FIGS. 3A and 3B show cross-sectional views of apparatus 200 from the perspective of lines A and B in FIG. 3, respectively. In FIG. 3A, catheter device 210 is shown, having a guide catheter lumen 232, two energy transmission member lumens 234 and a vacuum lumen 236. As shown in FIG. 3B, guide catheter 220 includes an expandable element lumen 238. Guide catheter lumen 232 may sometimes be configured with an inner diameter (or "profile") that is shaped (or "keyed") to allow guide catheter 220 to pass easily through lumen 232. This feature is demonstrated in FIGS. 3A and 3B, where guide catheter 220 and guide catheter lumen 232 each have an ovoid shape.

In general, catheter device 210 comprises an elongate, flexible catheter which may be advanced through the vasculature of a patient to a position in the heart for treating a defect. Thus, catheter device 210 may have any suitable length, diameter, cross-sectional profile and the like, and may be constructed of any suitable material. Tissue apposition member 212 (or multiple tissue apposition members in some embodiments) is disposed at or near the distal end of catheter device 210. Although many different types of devices may be used to bring tissues of the defect together, in one embodiment (shown in FIG. 2) tissue apposition member 212 comprises a defect covering member. defect-covering tissue apposition member 212 may be positioned to contact adjacent PFO tissues to fully cover, or block, the opening of the defect. In the case of treating a PFO, this blocking of the PFO may prevent right-to-left shunting of blood and may allow blood pressure in the left atrium to bring the septum primum and septum secundum at least partially together to close the PFO. Therefore, simply by forming a seal or blockage over the PFO, tissue apposition member 212 may help bring the PFO tissues together to assist in PFO closure.

To optimize use, the device of the present invention is typically positioned so as to best treat the defect tissue. In addition, the device typically apposes or approximates the tissue to be treated to allow a "weld" or fusion to occur. Such positioning and tissue apposition may be achieved in a variety of ways, including those described herein. In the embodiment shown in FIG. 3, tissue apposition member 212, especially when configured as a PFO-covering member, may be collapsible/expandable to facilitate advancement and delivery of catheter device 210. For example, tissue apposition member 212 may comprise a collapsible polymeric cover disposed over an expandable/collapsible frame. In other embodiments, tissue apposition member 212 may be constructed of a shape memory material, such as nitinol or another shape memory metal, spring stainless steel or the like, to allow catheter device 210 to be delivered through vasculature and then allow tissue apposition member 212 to expand to contact and appose the PFO tissues. In some embodiments, catheter device 210 and tissue apposition member 212 may be delivered to a location for PFO treatment through an introducer sheath. To further enhance the use of apparatus 200, an angle between catheter device 210 and tissue apposition member 212 may be selected to approximate a convenient angle for delivery and/or deployment. In one embodiment, for example, the angle between catheter device 210 and tissue apposition member 212 may approximate the angle between the inferior vena cava and the interatrial septum. Any other configuration, combination of angles and the like is contemplated, however. In some embodiments, for example, direct steering of the angle of tissue apposition member 212 relative to catheter device 210 may be employed to enhance delivery of catheter device 210 to a treatment site.

In this and other embodiments, tissue apposition member 212 may also include one or more vacuum members for applying vacuum to the defect tissues or those surrounding the defect. In one embodiment, for example, suction lumen 236 (FIG. 3A) may extend from the proximal end to the distal end of catheter device 210, opening into one or more vacuum-application apertures at the distal end of tissue apposition member 212. The vacuum-application aperture(s) may have any suitable configuration, such as a continuous aperture encircling tissue apposition member 212, multiple apertures encircling tissue apposition member 212 or in any other suitable configuration at or near its distal end, or the like. In still another embodiment, vacuum may be applied via a large, central lumen in tissue apposition member 212. In any case, vacuum force may be used to bring tissues together and/or to secure tissue apposition member 212 and thus catheter device 210 to the tissues.

To further facilitate use and positioning of apparatus 200, catheter device 210 may include one or more radiopaque markers 226 for facilitating visualization of the device 210. Catheter device 210 may also include a "flexible isolation portion" 228, which in some embodiments comprises a rigid but shapeable portion disposed toward the distal end of catheter device 210, between tissue apposition member 212 and the generally flexible proximal portion of catheter device 210. Flexible isolation portion 228 may help to isolate tissue apposition member 212 from some or all movement experienced by the more flexible, proximal portion of catheter device 210, thus allowing a PFO treatment procedure to be performed without significant movement of tissue apposition member 212. In other embodiments, flexible isolation portion 228 may be more flexible than the more proximal portion of catheter device 210, thus enhancing maneuverability, shapability or the like of the position of tissue apposition member 212 relative to the more proximal portion.

Guide catheter 220 is generally a flexible catheter along which catheter device 210 may be slidably advanced to a position for defect treatment. Guide catheter 210 is configured to fit at least partially within or against the defect, and optionally through the defect such as into the left atrium of the heart when treating a PFO. Optionally, one or more radiopaque markers 224 may be included on guide catheter. Guide catheter 220 may contain one or more expandable members 222 or other similar devices for expanding within the defect to help bring the defect tissues together, anchor catheter device to the defect tissues, or both. As shown in FIG. 3, for example, a "fish mouth" or two-prong expandable member 222 may be deployed within a PFO. When the two arms of the fish mouth separate, PFO-adjacent tissues are stretched laterally such that they tend to come together in the middle. In some embodiments, expandable members 222 may assist in PFO tissue apposition either while extending into the left atrium, while in other embodiments expandable members 22 do not extend into the left atrium.

Expandable member 222 may have any suitable configuration and may be constructed from any suitable materials. For example, expandable member 222 may be spring loaded, made of shape memory material, such as nitinol or spring stainless steel or the like. Alternatively, expandable member 222 may be expanded mechanically by one or more expansion members coupled with expandable member 222 and controlled via an actuator at the proximal end of guide catheter 220. During delivery of guide catheter 220, expandable member 222 reside within guide catheter 220. Guide catheter 220 may then be withdrawn to deploy expandable member 222 either within the defect or in the case of a PFO treatment, within the left atrium to be drawn back into the PFO. In some embodiments, expandable member 222 has one or more preshaped or shapeable distal tips 223. Tips 223 may be used, for example, to help locate and cross the defect. In the case of treating a PFO for example, tips 223 may also be used to contact a left atrial surface of the septum primum or other PFO tissue, so that when the expandable member 222 is pulled proximally tips 223 help bring the PFO tissues together and/or anchor apparatus 200.

In some embodiments, one or more expandable members 222 may include or be coupled with one or more energy transmission members. For example, expandable member 222 may include one or more radiofrequency transmission members for monopolar or bipolar RF transmission. A fish mouth expandable member 222, for example, may include a bipolar RF transmission member on each prong of the fish mouth. In some embodiments, energy transmission members may be included in or coupled with both expandable member 222 and tissue apposition member 212. In any such embodiments, some portions of the energy transmission member(s) may be insulated, to prevent unwanted energy transmission to tissues. For example, in some embodiments a distal tip extending to contact a left atrial surface of PFO tissues may be insulated to prevent energy transmission from the tip.

Referring now to FIG. 4, an alternative embodiment of a PFO-treatment apparatus 300 suitably includes a catheter device 310 having a tissue apposition member 312, radiopaque marker 326 and flexible isolation portion 328. For exemplary purposes only, this embodiment is shown having one energy transmission member 314, such as a monopolar RF transmission member. As shown, apparatus 300 may also include a guidewire 320, over which catheter device 310 may be advanced. Guidewire 320 includes a split, expandable portion 322, which may be released from catheter device 310 to expand within a PFO to bring PFO tissues together. Guidewire 320 also suitably includes a distal tip 323 for locating and crossing a PFO and/or for contacting a left atrial surface of the septum primum or other PFO tissue.

Apparatus 300 may include any of the features described above in relation to FIG. 3. In the embodiment in FIG. 4, apparatus 300 does not include a guide catheter, but instead includes guidewire 320. Guidewire 320 may serve many or all of the functions of the guide catheter and expanding member described above in reference to FIG. 3. Split portion 322 of guidewire 320 may be constructed of shape memory material or other suitable materials to allow it to expand when released from catheter device 310. Additionally, split portion 322 may include or be coupled with one or more energy transmission members instead of or in addition for energy transmission member(s) 314 coupled with tissue apposition member 312. Guidewire 320 may also include one or more distal tips 323, which again may be used to locate and cross a defect and/or to help appose defect tissues. In some embodiments, tip 323 may also include or be coupled with one or more energy transmission members.

Referring now to FIGS. 5A and 5B, another embodiment of a defect-treatment apparatus 400 suitably includes a catheter device 410 having a tissue apposition member 412, radiopaque markers 426 and flexible isolation portion 428. As shown, apparatus 400 may also include a guidewire 420, over which catheter device 410 may be advanced. Guidewire 420 includes a split, expandable portion 422, which may be released from catheter device 410 to expand within a defect to bring defect tissues together. Guidewire 420 also suitably includes a distal tip 423 for helping locate and cross the defect and/or for contacting a left atrial surface of the septum primum or other defect tissue to help bring the defect tissues together. In this embodiment, catheter device 410 also includes a braided portion 430 which includes the proximally-disposed tissue apposition member 412 and a more distal energy transmission portion 432, the latter of which is coupled with energy transmission members 414. Tissue apposition member 412 and energy transmission portion 432 may be a unitary braided member, with tissue apposition member 412 configured to cover energy transmission portion 432 in a retracted position and to provide vacuum force application.

In use, catheter device 410 is typically advanced over guidewire 420 to a treatment location. Split portion 422 and optionally distal tip 423 are then used to help appose the tissues adjacent the defect. Before, during or after retraction of guidewire 420, energy transmission portion 432 is retracted into tissue apposition member 412. Defect tissue is then brought together using tissue apposition member 412, and energy is transmitted to the tissues using energy transmission portion 432. In some embodiments, tissue apposition member 412 provides for application of vacuum energy to the tissues to suction the tissues at least partially into tissue apposition member 412, thus enhancing contact of the tissues with energy transmission portion 432. Energy transmission portion 432 may comprise, for example an electrode mesh material, while tissue apposition member 412 may comprise an elastic coated mesh or other material. Again, any features described above in reference to other embodiments may be applied to the embodiment shown in FIGS. 5A and 5B.

With reference now to FIG. 6, another embodiment of a defect-treatment apparatus 500 suitably includes a catheter device 510 having a tissue apposition member 512, energy transmission members 514, radiopaque marker 526 and flexible isolation portion 528. For simplicity, apparatus 500 is shown without a guide catheter or guidewire, though either may be included. In this embodiment, tissue apposition member 512 includes ribs or "bellows" 540 to facilitate placement and/or alignment of tissue apposition member 512 relative to the septal wall tissues to be treated and/or to enhance adherence of apparatus 500 to the septal wall. For example, ribs 540 may allow catheter device 510 to move relatively freely relative to tissue apposition member 512, without displacing tissue apposition member 512 from the defect tissues.

Referring now to FIG. 7, another embodiment of a defect-treatment apparatus 600 suitably includes a catheter device 610 having a tissue apposition member 612, energy transmission members 614, radiopaque marker 626 and flexible isolation portion 628. Apparatus 600 is shown without a guide catheter or guidewire, though either may be included. In this embodiment, tissue apposition member 612 includes multiple struts 650 covered by a covering 652, which may comprise a polymeric covering or any other suitable material. Struts 650 may be self-expanding or may open via a mechanical opening actuator coupled with struts 650, such as opening apparatus used to open an umbrella. Energy transmission members 614 are coupled with self-expanding struts 650 on the internal surface of tissue apposition member 612, so as to contact defect tissue that is pulled within tissue apposition member 612, such as by applied vacuum force and/or by blood pressure from the left atrium.

II. Application of Energy

Generally, devices of the invention apply energy tissues using one or more energy transmission members (ETM). Such ETMs are typically described as electrodes, such as RF electrodes, for example as electrodes 214, 313, 314, 1213, 1313. In various embodiments, however, an ETM may comprise any of a number of devices and may transmit any suitable type of energy for closing a n anatomic defect. Some types of energy which may be used, for example, include radiofrequency, cryogenic, resistive heat, ultrasound, microwave and laser energy. Radiofrequency ETMs may be either monopolar or bipolar, with monopolar catheter devices also including a grounding member. Energy transmission members may have any suitable configuration. For example, they may have a curved shape to approximate a radius of curvature of the defect, as shown in FIG. 3, or they may be configured as points for spot-welding the defect tissues, as a circular member for welding around the circumference of defect tissues, as one or more mesh or braided members disposed within the orifice of tissue apposition member 212 or the like. Furthermore, ETM may take the form of a planar electrode such as those shown in FIGS. 2D-2G". In some embodiments, ETMs are fixedly coupled with tissue apposition member 212, while in other embodiments ETMs are movable within tissue apposition member, for example to move about the circumference of the defect to weld defect tissues at multiple locations.

Referring again to FIGS. 2C and 2D, one form of ETM comprises a planar electrode 1313, which may have any suitable configuration and be made of any suitable material(s) in various embodiments. Electrode 1313 may also be attached to vacuum housing 1312 by any suitable means, such as adhesives, welding or the like. In one embodiment, electrode 1313 may include one or more attachment members, such as prongs or the like, which extend from the planar surface of electrode 1313 and are embedded in or attached to a surface of housing 1312. Planar electrode 1213 may comprise any suitable metallic material such as Nitinol, Elgiloy®, titanium, platinum, cobalt chromium, stainless steel or spring steel or other resilient material and be a wire mesh, a flexible circuit, a patterned metallic surface, or the like. Planar electrode 1213 may be formed from a single sheet, by being laser cut, photochemically etched, electron-discharge machined (EDM) or other useful processes known in the art. Furthermore, planar electrode 1213 may be plated or surface treated to be radiopaque and/or echogenic. Such plating may also allow for improved current conduction, and may be useful to create variable thickness electrodes that provide different current conductivity along the surface of one electrode. Platings or coatings may also serve as a "non-stick" surface to minimize tissue or blood debris from accumulating on the electrode.

Electrode 1213 also includes a guidewire port or ports 1214 for passage of a guidewire 1211. Guidewire port 1214 may be centrally located on the electrode face, or offset depending on the desired approach to the defect. The outlet of guidewire port 1214 may have a counter-bored, chamfered or rounded leading edge to provide for smooth guidewire passage. In various embodiments, electrode 1313 may have one or more than one guidewire port 1314. Is some cases, guidewire port 1314 is centered on electrode 1313, while in other embodiments, one or more guidewire ports 1314 may be located off-center on electrode 1313 as in FIG. 2C. Off-center or eccentric guide ports 1314 may facilitate localization and/or positioning of housing 1312 relative to a tissue defect such as a PFO, and may assist in the collapsibility of the housing 1312 for deployment purposes. Guidewire port 1314 may be an aperture in the electrode face, and may be further formed of a lumen or hypotube 1315 that extends into the catheter body to allow the operator to easily exchange guidewires, or insert guidewires at separate points during the procedure as desired. It may be desirable to form the guidewire port 1314 to include a ramp 1314a to predetermine the angle of outlet of the guidewire so that it exits at the desired trajectory. Alternatively, a guidewire 1311 with an expandable balloon may be used to inflated within a tissue defect or beyond in the heart chamber (e.g. right atrium) to bias vacuum housing 1312 in a desired direction. It is also within the scope of the present invention to incorporate a balloon on the catheter shaft or guide to achieve a similar purpose.

FIG. 2G' further depicts a thermocouple (TC) and the electrical connection wire (EC) that can be fixed to the face of electrode 1313. Such connection may be integrally formed as part of the electrode fabrication (e.g. leaving material to form a landing site for the wires to be connected during electrode fabrication.) To accommodate all the functions described herein, catheter shaft 1310 includes one or more guidewire lumens 1342, an electrode lumen 1343, a thermocouple lumen, and an infusion port 1344. Vacuum may be applied through a separate lumen (not shown) or the annular space 1345 within the catheter body.

As mentioned earlier, the phrase "tissue welding" herein is used to mean application of energy to (or removal of energy from) defect tissues to substantially and acutely close the defect. Energy transmission members generally provide for transfer of energy to or from PFO tissues to denature collagen in the tissues, and when the collagen is allowed to renature, with the tissues apposed, the once separated tissues bind together to form a stable tissue bridge. This stable tissue bridge substantially and acutely closes the PFO, preferably permanently. PFO tissues may, in some embodiments, be brought and held together by one or more tissue apposition members 212. Energy transmission members provide sufficient energy transfer, for a sufficient time, to weld the tissues. The time span of energy transmission may be, for example, from about 0.5 seconds to about 15 minutes, and more preferably from about 30 seconds to about 5 minutes. Energy transmission, in some embodiments, may be from about 0.5 Watts to about 100 Watts, and more preferably from about 2 Watts to about 40 Watts. Any other suitable energy and timing combination may also be used. In one experimental example, a PFO in a section of pig heart tissue used ex-vivo in a flowing saline test fixture was closed by applying suction to appose the PFO tissues and applying RF energy at approximately 25 watts for 7 minutes. RF energy application was then discontinued, but suction was continued for an additional 1 minute to keep tissues in apposition while the tissue cooled, to allow collagen in the tissues to reorganize and bind together to form a stable tissue bridge. Many other energy amounts, energy application times, tissue apposition times and the like are contemplated, however. Similarly, in the event that devices of the present invention are employed for ablation of EP defects, a variety of temperature, power and time combinations may be used.

Although any type of energy may be transmitted by ETMs, some embodiments will make use of monopolar or bipolar RF energy. Devices may use monopolar radiofrequency energy, for example, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on apparatus 200. Further embodiments may include applying bipolar energy between two or more ETMs, which are electrically isolated from one another within catheter device 210.

Control systems coupled with ETM or tissue apposition member 212, or otherwise disposed within apparatus 200, may sense an amount of energy delivered to PFO tissues and, optionally, may automatically stop energy delivery upon detecting a change in condition of energy delivery, for instance an increase in electrical resistance or impedance or rate of change in impedance, in PFO tissues or in apparatus 200, an increased energy draw from the treatment apparatus, and/or the like. In some embodiments, energy delivery may be automatically stopped when an amount of delivered energy reaches a desired level, such as an amount of energy sufficient to substantially close the PFO. The amount of delivered energy may be monitored by any suitable method, such as monitoring temperature or impedance in PFO tissues or the like. In some embodiments, one or more sensors coupled with tissue apposition member 212, ETMs, or any other part of apparatus 200 may be used for monitoring such indicia. Examples of sensor devices include but are not limited to infrared sensing devices, thermistors and thermocouples. A control system may also include a microprocessor coupled with the sensors to determine when a desired amount of energy has been delivered and/or to automatically stop energy transmission. In alternative embodiments, a microprocessor may be included in apparatus 200 which can sense, monitor and control energy delivery, thus not requiring separate sensors.

III. Method of Treatment

FIGS. 8A-8E demonstrate a method for treating a PFO according to one embodiment of the present invention. It should be emphasized that this is merely one possible embodiment, and that many alternative methods are contemplated. For example, steps may be modified, repeated, added or deleted from the method, the order of steps may be changed, and/or the like, without departing from the scope of the invention as defined by the appended claims. Therefore, the foregoing description should not be interpreted to limit the scope of the invention in any way.

Figure 8A:
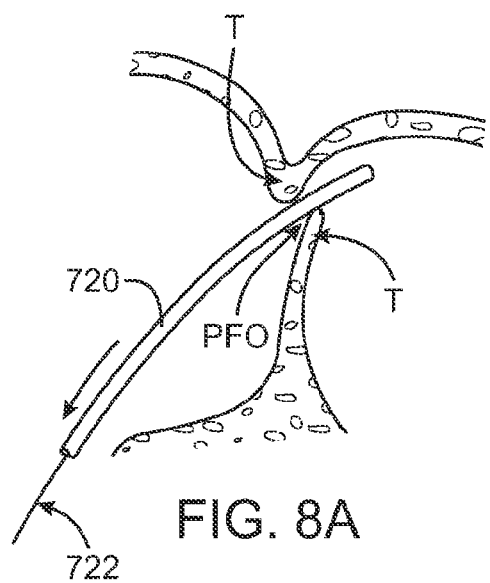
Figure 8B:
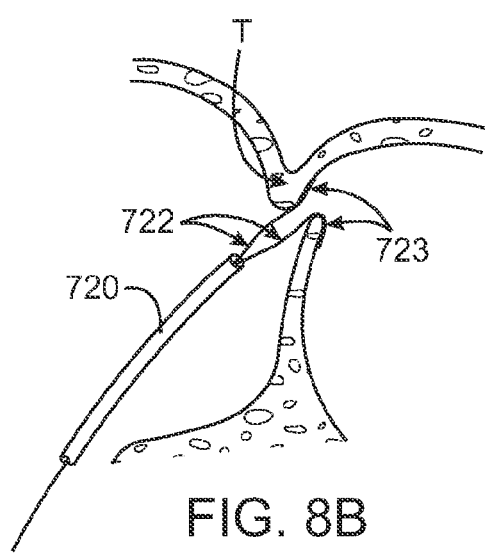

That being said, in one embodiment, a PFO treatment method includes advancing a guide catheter 720 through the PFO, between tissues T adjacent the PFO, the guide catheter 720 containing an expandable member (FIG. 8A). Guide catheter 720 is then retracted (proximally pointing arrow) to expose expanding member 722 (FIG. 8B). Expanding member 722 may be exposed/expanded within the PFO, or may alternatively be exposed/expanded within the left atrium and pulled back into the tunnel of the PFO. Expanding member 722 may also include one or more distal tips 723, which may help to locate the PFO, cross the PFO, appose the tissues T and/or to anchor guide catheter 720 to the tissues T.

Figure 8C:
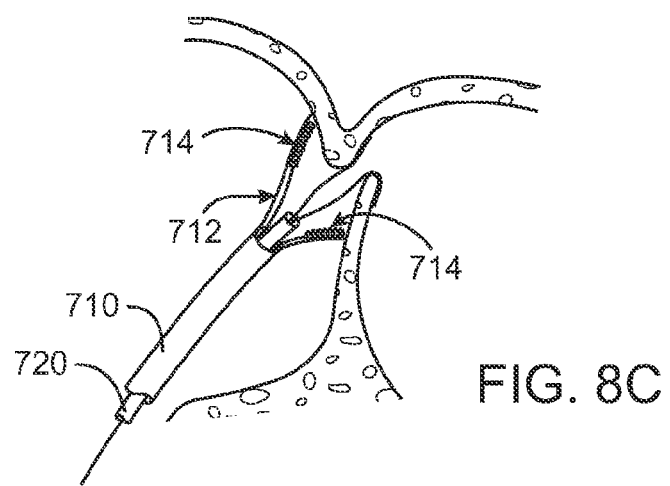
Figure 8D:
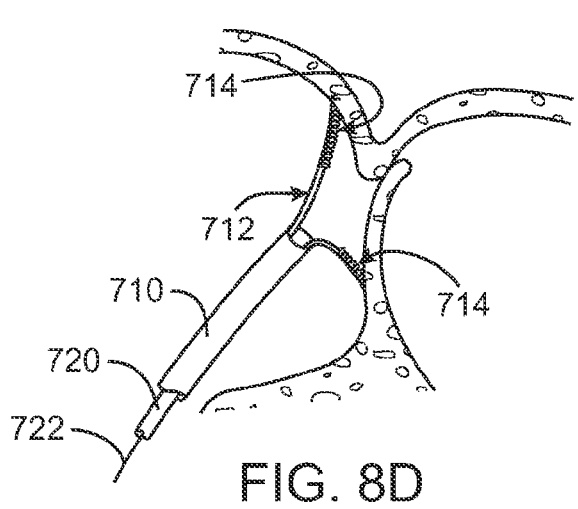
Figure 8E:
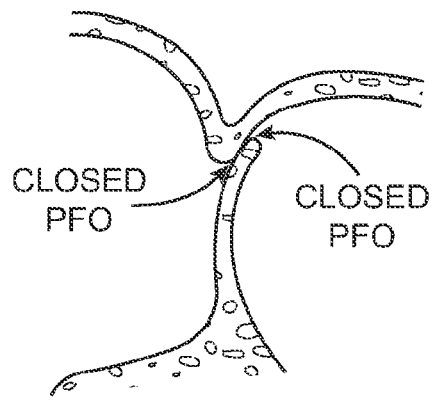

Once guide catheter 720 is in place and expandable member 722 is deployed, catheter device 710 may be advanced over guide catheter 720 to a position for treatment of the PFO (FIG. 8C). Catheter device 710 typically includes a tissue apposition member 712 (shown here in cross-section for clarity) and one or more energy transmission members 714. Suction may be applied using tissue apposition member 712, left atrial pressure may be used, or both, to bring tissues T adjacent the PFO together (FIG. 8D). Once tissue apposition member 712 is placed and/or activated, guide catheter 720 and expandable member 722 may be removed through catheter device 710, leaving the tissues T apposed and catheter device in place, as in FIG. 8D. Alternatively, guide catheter 720 and expandable member 722 may be left in place during a first welding to close the majority of the PFO and then removed. The small patent portions of the PFO remaining after the guide catheter 720 and expandable member 722 are removed may then be closed by a second weld or may be left open and allowed to close via healing or scarring. Tissue apposition member 712 may be used to hold tissues T together before, during and/or after energy transmission members 714 weld the tissues T together. Such holding of the tissues together and application of energy to weld the tissues may be performed for any suitable time, such as for less than one second to many minutes. Once a sufficient amount of energy has been applied to the tissues T to acutely close the PFO, catheter device 710 is removed, leaving a closed PFO, as in FIG. 8E.

Figure 9A:
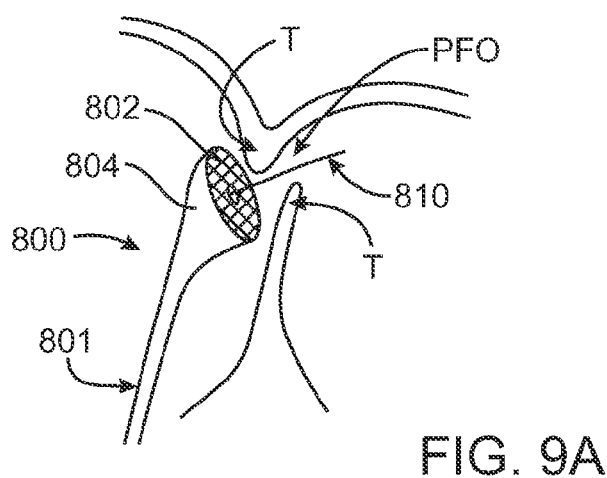

FIGS. 9A-9E demonstrate another embodiment of a method for treating a PFO. Such a method may also be used to treat other anatomic defects in human tissue, as discussed previously. In FIG. 9A, a tissue treatment device 800 including a catheter body 801, a vacuum application member 804 and an electrode 802 is advanced along a guidewire 810 to a position near tissues T adjacent the PFO. Using any of a number of different techniques, such as advancing device 800 over an eccentrically positioned guidewire 810, actively steering a distal end of device 800, visualizing device 800 using radiopaque markers and flouroscopy or endoscopic devices such as flexible scopes, and/or the like, device 800 is generally positioned over the PFO.

Figure 9B:
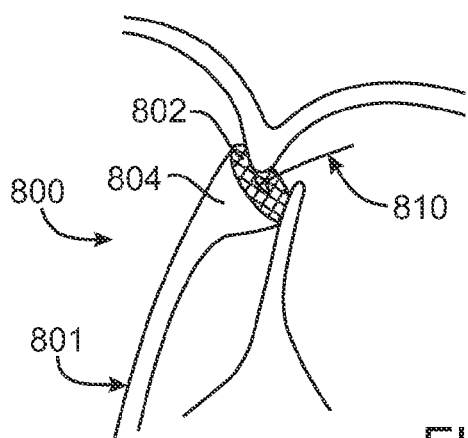
Figure 9C:
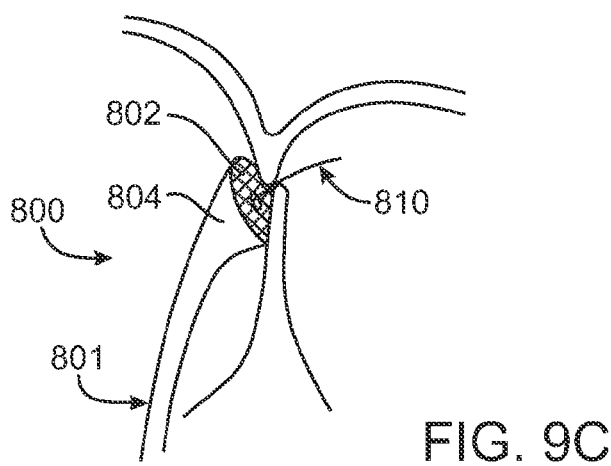

Next, as shown in FIG. 9B, device 800 is engaged with the PFO adjacent tissues T. A seal may be formed at this point between the distal end of device 800 and the tissues T. As shown in FIG. 9C, vacuum force may then be applied via vacuum application member 804 to present the tissue to be treated up against the electrode face such that the tissue T and the face of the electrode have a substantially common plane. For purposes of this disclosure, the phrase "substantially common plane" means that the tissue T is held flat against the surface of the electrode. While such a presentation may not be exactly "flat" or "planar," to account for various tissue imperfections or the fact that tissue may protrude into the interstices of the electrode face, the design of the electrode catheter facilitates an approach to the tissue T "en face," or leading with the face of the electrode. Although other presentations are anticipated by the present invention, such an "en face" presentation may be advantageous not only because it presents the defect in a closed manner (e.g. in the case of a PFO the flap is flattened against the electrode surface), but also because it allows for efficient energy transmission to the tissue T (flat application surface can work to produce a more uniform surface thickness), thereby closing or treating the defect in a desirable treatment time.

Once the tissues T are contacted with the electrode, energy may be applied to the tissues T via electrode 802. In some embodiments, vacuum force may first be stored in a reservoir and may then be applied to the tissues T as an impulse of vacuum to quickly form a seal and thereby minimize loss of blood from the patient. The vacuum force applied ensures that the flap of the defect furthest from the vacuum application member is snugly apposed with the flap nearest thereto. In addition, in cases where the defect is an opening and not a flap, applied vacuum force is typically sufficient to bring the tissues to be sealed in contact with each other. A number of PFO defects are accompanied by aneursysmal disease. In some embodiments, in addition to treating a PFO a method may also tighten or reinforce the septum of the heart, thus also treating the aneurysmal disease.

In some embodiments, irrigation fluid may be circulated through device 800 to irrigate the area of energy application to the tissues T. Such irrigation fluid may be circulated within vacuum housing 804, for example, by introducing fluid through a lumen of device 800 and then using the vacuum force to bring the fluid back into the lumen. In some instances, fluid flushing is used to prevent clotting and/or blood accumulation in housing 804. For this purpose a nonconductive fluid such as heparinized D5W may be used. In addition or alternatively, saline may be used to prevent clotting within the patient and/or device 800 (e.g., electrode housing, catheter lumen(s), or the like). Saline may also be employed to affect the heating characteristics of the desired treatment. Infusion may also act to cool the tissue interface, thereby preventing rapid tissue necrosis.

The procedure may be monitored in several ways. In some embodiments, the fluid brought back through device is monitored for color, to determine when there is little or no blood in the fluid, thus helping to determine when a seal has been acquired and/or the PFO is closed. It may also be desirable to measure the impedance of the treatment region to determine if a seal is being maintained (impedance of blood is lower than tissue, so a change may indicate the presence of blood (leak) or lack of seal). Alternatively, an optical detector may be employed to control vacuum and shut off the force if blood is detected in the evacuated fluid. Similarly, the rate of extraction of fluid may be monitored and calculated to ensure that the rate of extraction equals that of infusion. In many cases, it may be sufficient to infuse fluid "passively" (from an IV fluid bag), e.g. gated by the rate of vacuum, to form a "closed loop" system where the rate of suction and aspiration maintain a seal on the defect site to allow the thermal energy treatment of the site. For safety purposes, a suction lock apparatus as is known in the art, may be employed on the proximal end of the catheter to ensure that fluid is not inadvertently extracted from the patient. Alternatively, the rate of extraction of the fluid from the supply reservoir (e.g. an IV bag) may be monitored to detect whether or not a seal against the tissue has been achieved. If a seal is achieved, the flow rate from the reservoir will increase. If a seal has not been achieved, or has been lost, passage of blood into the housing will predominate, slowing the flow rate from the reservoir.

Figure 9D:
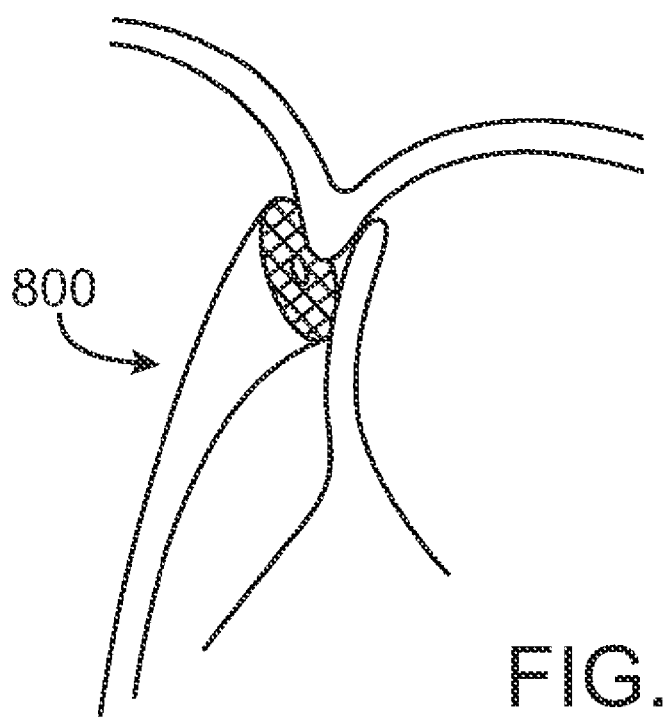
Figure 9E:
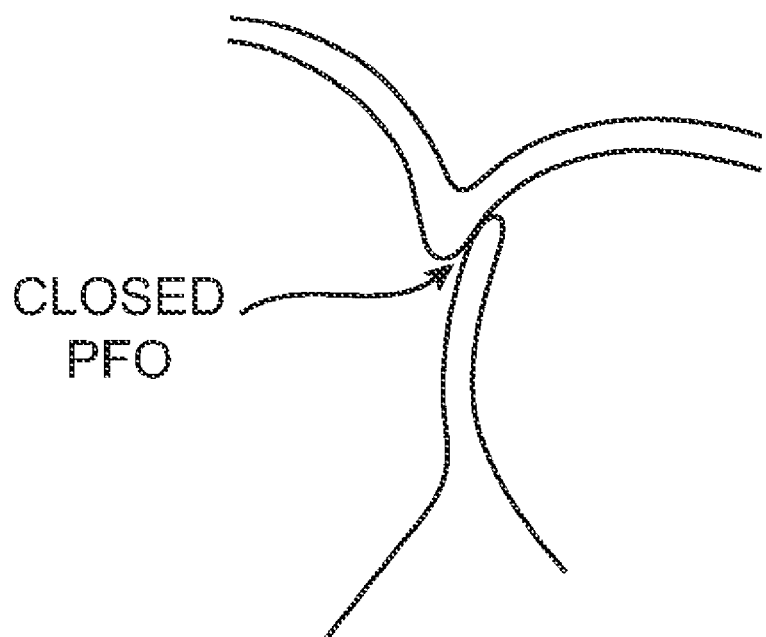

In FIG. 9D, the PFO has been closed and guidewire 810 has been withdrawn. In some embodiments, guidewire 810 is withdrawn after energy is applied and the PFO is closed, thus leaving a small hole in the closed PFO where guidewire 810 used to reside. Nevertheless, the PFO is still substantially closed, and the small hole left by guidewire 810 will typically close naturally, due to scarring. Finally, in FIG. 9E, device 800 is removed, leaving a substantially closed PFO. After the defect is closed, it may be desirable to maintain apposition of the defect tissue while tissue cools back down to body temperature, although this is not necessarily required for effective tissue bonding. In addition, it is within the scope of the invention to perform multiple applications of the energy device to treat the defect. This can be particularly advantageous with larger defects, or defects that present varied tissue thicknesses. Also contemplated by the present invention is the use of the device multiple times, or re-treating a defect that may re-cannulate following the initial treatment at a time period separate from the initial treatment.

The foregoing devices are particularly appropriate for welding of tissues where a device can be applied against two layers of tissue with or without suction as described above. However, some tissue defects, such as ASDs, VSDs, and similar defects, have a hole which must be closed. This means that the tissue must first be drawn into apposition either by vacuum or mechanical approximation before applying energy to weld those tissues together. One device which would be effective in drawing the tissues surrounding such an opening together was described in U.S. patent application Ser. No. 10/811,228 filed Mar. 26, 2004, which was previously incorporated by reference. This device described a tubular expandable clip with multiple distal-facing tines, mounted around an expandable tubular balloon. The balloon could be positioned in the defect and inflated until the balloon diameter is as large as the defect, while the clip and tines are proximal to the defect. The balloon and clip could then be advanced through the defect until the tines of the clip pierce the tissue surrounding the defect. The balloon could then be deflated, causing the clip to also contract radially, gathering the tissues together. Energy would then be applied to the tissue, either using the clip itself as the electrode, or an electrode on the surface of the balloon, or an entirely separate electrode. This energy would serve to weld the tissues in their gathered state. After welding, the balloon and clip could be withdrawn from the tissue, leaving the welded defect with little or no residual opening. This is only one exemplary device which could be used to draw the tissue surrounding an opening in a tissue structure together in order for the purpose of welding the tissue together. A PDA might also be closed using the balloon device described in the material incorporated immediately above, which would gather the tissue of the walls of the PDA together before applying energy.

As mentioned above, the foregoing method may be altered in any number of ways without departing from the scope of the invention. In some embodiments, for example, tissues adjacent the defect are brought at least partially together and energy is applied to the tissues to acutely close the defect with fewer steps and/or fewer device components than just described. For example, application of suction to appose tissues is not required in all embodiments. Furthermore, a variety of different types of energy may be applied to the tissues from a variety of differently configured energy transmission devices. In some embodiments, one or more of the steps described above may be repeated one or more times, such as by repeating a tissue welding step. The above description, therefore, is provided for exemplary purposes only.

IV. Catheter Device Additional Features

As is described above, and with reference now to FIG. 10, in one embodiment, a distal end of a catheter device 40 for treating anatomical tissue defects includes a housing 46, an electrode 51 coupled with housing 46, multiple struts 47 (or "attachment members") for attaching electrode 51 to housing 46 and providing support, a radiopaque marker 48 for attaching struts 47 to housing 46 and promoting visualization, and a sheath 42 through which housing 46 and electrode 51 are delivered to a location for performing a procedure. As will be described further below, housing 46 and electrode 51 are typically collapsible, so as to fit within and be passable through sheath 42. Both housing 46 and electrode 51 may be given any of a number of different features to provide for collapsibility. For example, resilient materials may be used, some portions of housing 46 and electrode 51 may be structurally weaker than other portions to promote folding or collapsing along the weaker portions, or the like.

FIG. 11 shows an inferior view of housing 46 and electrode 51. Housing 46 generally includes a proximal neck portion 55 and a distal collapsible portion 56. Collapsible portion 56 may have any of a number of shapes, such as circular (as shown), ellipsoid, ovoid, rectangular, square, triangular, hexagonal, octagonal or the like. Neck 55 typically attaches proximally to a catheter body (not shown). In another embodiment, the catheter body may simply extend into housing 46, with the body and housing 46 being a single piece or extrusion. Electrode 51 generally includes an outer rim 53, multiple electrode struts 52 (or wires) extending from one side of rim 53 to the other, and a guidewire opening 54 within electrode struts 52 to allow for passage of a guidewire. Electrode 51 may have any of a number of configurations, and electrode struts 52 may be disposed in any suitable pattern, some of which are described in further detail below. Attachment member struts 47 are also shown. One embodiment includes five struts 47, four of which extend over the top of housing 46, and one strut 47' extending proximally along the inferior surface of neck 55. Inferior surface strut 47' thus typically is shorter and may have a different shape than other struts. In alternative embodiments, any number, shape and size of attachment struts 47 may be used.

Referring to FIG. 12, a cross-sectional side view of a distal end of a catheter device 60 shows a housing 61, an electrode 62 housed within housing 61, and a flexible foot 58 extending from housing 61 and configured to contact tissues adjacent a tissue defect. Foot 58 has a distal side 58a with shorter height than a proximal side 58b, this configuration facilitating tissue contact and formation of a vacuum seal on the tissue. A guidewire 64 may be passed through housing 61 and electrode 62 for guiding the catheter device to a location for performing a treatment procedure.

With reference now to FIG. 13, in another embodiment a catheter device 70 includes a housing 71 with a flexible foot 68 and a movable electrode 72 coupled with a movable energy delivery device 73. Movable electrode 72 is a planar, collapsible electrode that is free to move relative to housing 71. By moving energy delivery device 73, electrode 72 may be moved proximally, distally, superiorly and inferiorly (solid and hollow doubled-tipped arrows). Using such a movable electrode 72, a user may achieve a suction seal on tissue with housing 71, contact electrode 72 with tissue, apply energy to the tissue, and then move electrode 72 to another location within flexible foot 68 and apply more energy, without breaking the seal. In some embodiments, foot 68 may be substantially wider than electrode 72, allowing energy to be applied to multiple different sites using the same seal.

Referring to FIG. 14, in some embodiments a catheter device 80 includes a distal housing 81 (shown here with electrode removed for clarity) and a fluid infusion tube 88 coupled with an inner surface 82 of housing 81. Inner surface 82 includes multiple surface features 83, 84, 86 for directing fluid around housing 81 during a procedure. Generally, surface features include multiple ridges 83, depressions 84 (or channels) between ridges 83, and one or more fluid backstops 86. Backstop 86 prevents fluid exiting infusion tube 88 from backing up into infusion tube 88, and ridges 83 and depressions 84 help guide fluid around the inner cavity of housing 81 (see solid-tipped arrows). Ideally, infused fluid flows out of tube 88, around interior of housing 81, and back into a suction lumen 85 toward the proximal side of housing 81. Of course, ridges 83, channels 84 and backstop 86 may have any of a number of suitable shapes, sizes and numbers for directing fluid in a desired direction.

FIG. 15 shows an alternative embodiment of a catheter device 90 for treating anatomical tissue defects. In this embodiment, catheter device 90 includes a housing 94 and an electrode having multiple, discontinuous rim segments 92 and electrode struts 96 coupled with segments 92 and forming a guidewire opening 98. Using rim segments 92 instead of a continuous rim promotes collapsibility of both housing 94 and the electrode.

In other embodiments, and with reference to FIGS. 15A-15C, an electrode may generally have a fan shape and may be adapted to laterally collapse. By "laterally collapsible," it is meant that the electrode is adapted to collapse by having two opposite side draw closer to one another, similar to a collapsible, hand-held fan. In contrast, in embodiments of the device that do not laterally collapse, the electrode typically folds in on itself, with one lateral side of the electrode rolling or folding within the other side to allow the electrode and housing to fit within a sheath. Lateral collapsibility provides an alternative mechanism for collapsing the device.

Referring to FIG. 15A, in one embodiment, a laterally collapsible electrode 1460 includes electrode struts 1467, collapsible connecting elements 1466 disposed between struts 1467, and an outer rim 1463. In some embodiments, outer rim 1463 may be discontinuous, leaving one or more gaps 1464, which promote collapsibility of electrode 1460. In other embodiments, outer rim 1463 may be continuous. A housing 1461, in this embodiment, is also fan-shaped. The laterally collapsible electrode 1460 may be retracted into (and deployed from) a sheath 1462.

In an alternative embodiment, with reference to FIG. 15B, a laterally collapsible electrode 1470 may include only a plurality of branching electrode struts 1477, housed in a housing 1471. This embodiment does not include an outer rim or connecting elements, thus further promoting lateral collapsibility. On the other hand, electrode 1470 may not be as stable as the electrode 1460 in FIG. 15A. In another embodiment, shown in FIG. 15C, a laterally collapsible, fan-shaped electrode 1480 may be housed in a circular housing 1481. Electrode 1480 includes electrode struts 1487 and connecting elements 1486. In alternative embodiments, electrode 1480 may also include a continuous or partial outer rim.

In yet another embodiment, shown in FIGS. 15D (bottom/inferior view) and 15E (side view), a distal end of a catheter device 1430 may include a fan-shaped distal housing 1434 for promoting collapsibility. Fan-shaped housing 1434 is generally connected to a catheter shaft 1440 via a neck portion 1435. In some embodiments, as shown in FIG. 15B, neck portion 1435 may have one or more curves or bends 1437, which may in turn correspond to complementary curves or bends in a sheath 1442 of catheter device 1430. Bends 1437 generally facilitate placement, positioning, orientation and/or adjustment of housing 1434 before and/or during treatment. Included in housing 1434 are a flexible skirt 1432 for enhancing contact with tissue, multiple longitudinal electrode struts 1436 along which housing 1434 folds to collapse down into a convenient size for retracting into sheath 1442, a collapsible mesh 1438 disposed between struts 1436 and also allowing for lateral collapsibility, and a guidewire opening 1433. Again, in such a fan-shaped housing 1434, electrode struts 1436 can collapse laterally, thereby facilitating collapse of the structure by reducing it volumetrically, instead of folding the electrode on itself.

In one embodiment, and with reference now to FIGS. 15F and 15G, a distal end of a catheter device 1450 includes a sheath 1452 having an angled distal end 1454. Such an angled distal end 1454 may have any suitable angle, such as any angle less than 90°, and in some embodiments between about 30° and 60°. Angled distal end 1454 facilitates pushing a skirt 1457 of a housing 1456 of catheter device 1450 forward (see solid-tipped arrow in FIG. 15D). Angled distal end 1454 may also promote collapsing or folding of housing 1456, when housing 1456 is retracted back into sheath 1452, as will be described further below.

Referring now to FIGS. 16A-16E, a method for exposing and retracting a housing 1412 of a catheter device 1400 is demonstrated. As has been mentioned above, in one embodiment catheter device 1400 includes a sheath 1410 and a catheter body (not shown) movably disposed within sheath 1410. Coupled with (or extending from) the distal end of the catheter body is housing 1412, which is coupled with an electrode 1418 (or other energy transmission member). When catheter device 1400 is advanced intravascularly to a treatment location, housing 1412 is disposed within sheath 1410. When the distal end of catheter device 1400 is in a desired location, housing 1412 is exposed from sheath 1410, the procedure is performed, and housing 1412 is retracted into sheath 1410 for removal of device 1400 from the patient. Exposure and retraction of housing 1412 is typically accomplished by moving the catheter body axially relative to sheath 1410 and/or by moving sheath 1410 relative to the catheter body.

Figure 16A:
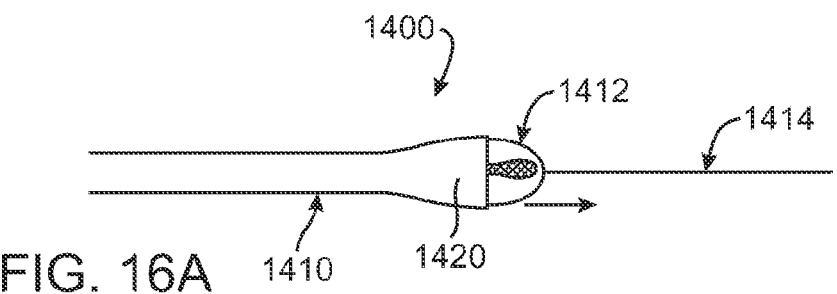
Figure 16B:
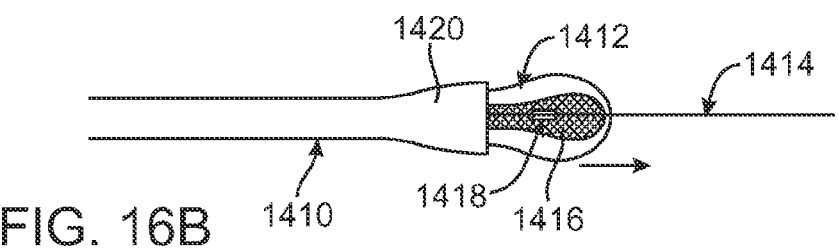
Figure 16C:
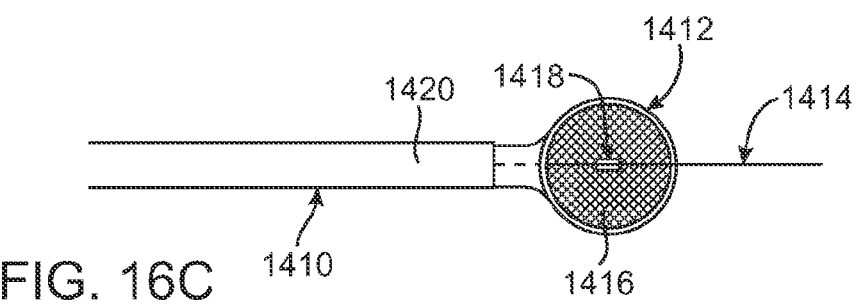
Figure 16D:
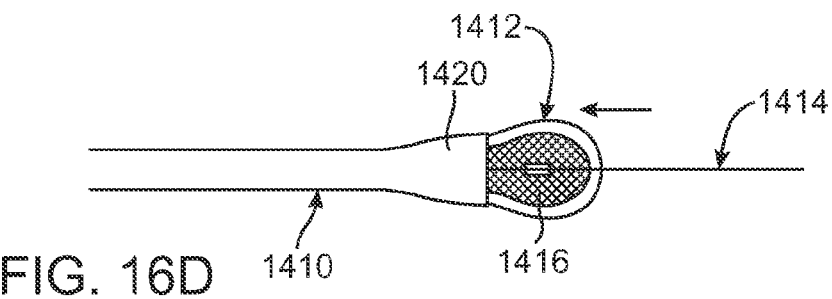
Figure 16E:
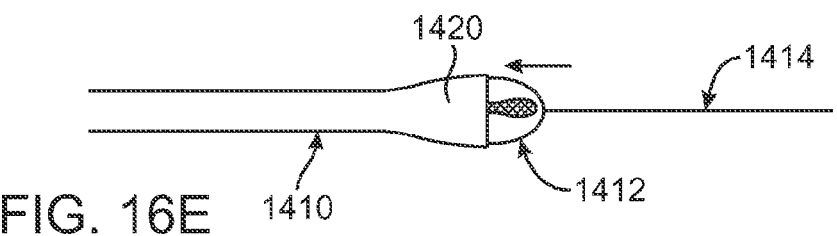

As shown in FIG. 16A, housing 1412 is disposed in sheath 1410 in a folded (or collapsed) configuration and is exposed from sheath 1410 by advancing distally (solid-tipped arrow) along a guidewire 1414. A flexible/expandable distal tip 1420 of sheath 1410 provides some amount of flexibility so that housing 1412 can begin to expand as it passes through tip 1420. In FIG. 16B, housing 1412 and electrode 1416 (with guidewire opening 1418) have been further exposed. In FIG. 16C, housing 1412 and electrode 1416 are fully exposed and ready to perform a procedure. After the procedure, housing 1412 is retracted, as shown in FIGS. 16D and 16E. Again, expandable tip 1420 helps to allow housing to fold or collapse as it is pulled proximally into sheath 1410. In some embodiments, as described above, tip 1420 may be angled or slanted to facilitate collapsing of housing 1412. Tip 1420, in some embodiments, may also be given a laterally-angled bias as well, so as to bias collapsing of housing 1412. For example, angling tip 1420 proximally from it left side to its right side may cause housing 1412 to fold first on its left side and then on its right side—i.e., the left side would fold into the right side. Such biased folding may allow for a smaller profile of housing 1412 when collapsed.

FIGS. 17-23 illustrate a number of different patterns and configurations for various embodiments of electrodes for use in a catheter device. These are by no means all the possible patterns and configurations and are offered primarily for exemplary purposes. In FIG. 17, for example, one embodiment of an electrode 1500 includes an outer rim 1510, electrode struts 1508 disposed within rim 1510, two guidewire openings 1512, and multiple attachment struts 1520. As mentioned above, an inferior-side attachment strut 1520' may be shorter and have a different configuration than other attachment struts 1520. Electrode struts 1508 are attached to rim 1510 at one or more attachment points 1514. In some embodiments, the number of attachment points 1514 is minimized, to enhance collapsibility of electrode 1500. Also in some embodiment, attachment points 1514 are positioned either at the same positions along rim 1510 as attachment struts 1520 or at positions as far away as possible from attachment struts 1520. This positioning helps reduce torque forces at attachment points 1514. Optional multiple guidewire openings 1512, with one off center opening 1512a, allows a user to select or change orientations of electrode 1500 relative to tissues during a procedure. Other embodiments may include only one guidewire opening 1512, which may enhance collapsibility/flexibility of electrode 1500. Yet other embodiments may not include any guidewire opening 1512, such as is a device used to treat anatomical tissue defects that do not have openings through which a guidewire would be passed.

Referring to FIG. 18, another embodiment of an electrode 1600 also includes an outer rim 1610, electrode struts 1608 disposed within rim 1610, two guidewire openings 1612, and multiple attachment struts 1620. In this embodiment, inferior-side attachment strut 1620' includes a divided portion 1621 where it attaches to rim 1610, which promotes collapsibility of electrode 1600 along its longitudinal centerline. An additional feature is a pair of matching bends 1622 in rim 1610, which also promote collapsibility of electrode 1600 along its longitudinal centerline.

FIG. 19 shows a similar embodiment of an electrode 1700, with an outer rim 1710, electrode struts 1708, two guidewire openings 1712, multiple attachment struts 1720, and a pair of bends 1722. In this embodiment, however, inferior-side attachment strut 1720' is asymmetric rather than divided. This asymmetric strut 1720' also promotes collapsibility.

In some embodiments, and with reference now to FIG. 20, it may be advantageous to provide for delivery of different levels of energy at different areas along an electrode 1800. In various embodiments, variable energy levels may be provided by any of a number of mechanisms or combinations thereof. For example, in some embodiments the configuration or pattern of the electrode may provide for variable energy delivery, as will be described further in reference to the embodiment shown in FIG. 20. In other embodiment, struts that form the electrode may be made of varying thickness along different portions of the electrode. In yet other embodiments, two or more energy delivery members may be coupled with one electrode, the energy delivery members being adapted to deliver different amounts of energy. In some embodiments, combinations of these mechanisms may be used. Variable energy delivery may be advantageous in treating various anatomical tissue defects, some of which will be asymmetrical, of varying thicknesses, and the like.

As already mentioned, FIG. 20 illustrates one embodiment of an electrode 1800 adapted for delivering variable amounts of energy to different areas of a defect. Electrode 1800 includes a rim 1810 and electrode struts 1808, without connecting elements between struts 1808, so as to promote collapsibility. In this embodiment, electrodes struts 1808 are formed generally as S-shaped members disposed longitudinally between opposite sides of rim 1810. Struts 1808 are not attached directly to one another, thus leaving spaces, forming lines of collapsibility 1824. At various points within electrode 1800, some S-shaped struts 1808 may be smaller 1826 and thus pack in more closely together (higher density), while larger struts 1828 may be less closely packed (lower density). Higher density 1826 and lower density 1828 areas on electrode 1800 may provide for energy transmission to tissues at different levels via the same electrode 1800, which may be advantageous in some embodiments, as discussed above.

Referring to FIG. 21, an alternative embodiment of an electrode 1900 providing variable energy delivery is shown. Electrode 1900 includes a rim 1910, electrode struts 1908, multiple connection points 1918 between struts 1908, and a guidewire opening 1916. Additionally, electrode struts 1908 are divided into two zones of energy delivery via multiple insulating members 1920. In an alternative embodiment, struts 1908 may instead be divided into energy delivery zones via gaps between the struts 1908. In the embodiment shown, a first energy delivery connection 1922 provides for delivery to one zone, and a second energy delivery connection 1924 provides for delivery to the other zone. Two separate energy delivery devices, such as wires, may be coupled with the connections 1922, 1924 to provide two different energy levels to the two zones. Again, this may be advantageous for applying energy to asymmetric, oddly shaped or varying thickness tissue.

In another embodiment, and with reference now to FIGS. 21A and 21B, a PCB layered electrode 1930 is constructed by encapsulating disconnected electrode surfaces by either heat sealing them between two insulating layers and then exposing the desired electrode surface, or potting them together with glue in the desired configuration. Electrode 1930 is coupled with multiple power wires 1932, for providing multiple different energy levels to various portions of electrode 1930. Disconnected electrode surfaces 1934, 1936, 1938 are encapsulated, with each surface being attached to a different wire 1932. In this way, variable power may be provided at different areas of electrode 1930. Surface 1934, 1936, 1938 are insulated from one another by encapsulating with insulating material. In another embodiment, glue may be used to isolate surfaces 1934, 1936, 1938. This is demonstrated in FIG. 21B, which shows a cross-section of a portion of an electrode 1940. Various electrode elements 1942 are separated either by heat sealing 1948 or glue 1950. Two power wires 1946, 1952 are shown, illustrating that different energy levels may be delivered to different regions of electrode.

Surfaces 1934, 1936, 1938 of electrode 1930 may have any suitable shape or configuration. In the embodiment shown, surfaces 1934, 1936, 1938 have a pattern generally radiating out from the center of electrode 1930, which may be advantageous due to the behavior of the current, which generates in a radial pattern. Additionally, the electrodes struts used to form surfaces 1934, 1936, 1938 may have any suitable thickness (short, solid-tipped arrows), and in some embodiments may have variable thicknesses. Any suitable combination of features for providing variable energy delivery is contemplated within the scope of the invention.

Referring now to FIG. 22, another embodiment of an electrode 2000 includes a rim 2010, struts 2008 connected at connection points 2018, a guidewire opening 2016, and multiple bends 2012 in rim 2010 to promote collapsibility.

FIG. 23 shows another embodiment of an electrode 2100, having densely packed electrode struts 2108 within a rim 2110, and a guidewire opening 2116. As is evident from this and the foregoing drawing figures, any of a number of suitable electrodes may be included in various embodiments of the present invention.

FIGS. 24A-24C show various embodiments of electrodes 2200, 2300, 2400 similar to that illustrated in FIG. 23, but with different shapes. Each electrode 2200, 2300, 2400 includes a plurality of separate, unconnected electrode struts 2208, 2308, 2408 and a central guidewire opening 2216, 2316, 2416. As is evident from these figures, electrodes 2200, 2300, 2400 may have any of a number of suitable shapes.

Although the foregoing description is complete and accurate, it has described only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. An apparatus for treating an anatomic defect in a heart, the apparatus comprising:
   an elongate catheter body having a proximal end and a distal end;
   a housing extending from the distal end of the catheter body for engaging tissues at a site of the anatomic defect;
   an energy transmission member adjacent to a distal end of the housing, the energy transmission member having at least one substantially planar surface, the housing being adapted to apply vacuum to the tissues to bring them together and position them against the energy transmission member; and
   a plurality of struts formed in a pattern, the struts being coupled to the housing,
   wherein the energy transmission member comprises an outer rim extending at least partially around an outer circumference thereof, and
   wherein at least some of the plurality of struts are attached to other struts as well as to the outer rim.

2. An apparatus as in claim 1, wherein the plurality of struts and the energy transmission member are of unitary construction.

3. An apparatus as in claim 1, wherein the struts comprise a metal.

4. An apparatus as in claim 1, wherein the plurality of struts comprise one or more markers to facilitate visual orientation of the energy transmission member relative to the anatomic defect.

5. An apparatus as in claim 4, wherein the markers comprise a radiopaque marker.

6. An apparatus as in claim 1, wherein the rim is discontinuous.

7. An apparatus as in claim 1, wherein the rim includes one or more inward bends directed toward the plurality of struts, the inward bends adapted to promote collapsibility of an electrode.

8. An apparatus as in claim 1, wherein the pattern in the plurality of struts includes at least one area of thicker struts relative to another area of thinner struts, such that different areas of the energy transmission member provide different amounts of energy transmission to the tissues.

9. An apparatus as in claim 1, wherein the pattern in the plurality of struts includes at least one fold line along which the energy transmission member folds to allow the energy transmission member to collapse.

10. An apparatus as in claim 1, wherein the struts are attached asymmetrically to the outer rim such that a first half of the housing and the energy transmission member fold into a second half of the housing and the energy transmission member when the housing and the energy transmission member assume collapsed configurations.

11. An apparatus as in claim 1, further comprising a plurality of metallic attachment members extending from the outer rim for attaching the energy transmission member to the housing.

12. An apparatus as in claim 11, wherein the plurality of metallic attachment members comprise:
   an inferior attachment member for attaching proximally to an inferior portion of the housing; and
   multiple superior attachment members for attaching proximally to a superior portion of the housing.

13. An apparatus as in claim 12, wherein the inferior attachment member extends onto an inferior portion of the catheter body, and the multiple superior attachment members extend onto a superior portion of the catheter body.

14. An apparatus as in claim 12, wherein the inferior attachment member divides before attaching to the outer rim at two attachment points.

15. An apparatus as in claim 12, wherein the inferior attachment member curves asymmetrically before attaching to the outer rim.

16. An apparatus as in claim 11, wherein the plurality of struts are attached to the outer rim at locations apart from attachment points of the attachment members to the outer rim.

17. An apparatus as in claim 11, wherein the plurality of struts are attached to the outer rim at attachment points of the attachment members to the outer rim.

18. An apparatus as in claim 1, wherein the anatomic defect comprises a defect selected from the group consisting of a patent foramen ovale, a ventricular septal defect, an atrial septal defect, a left atrial appendage, and a patent ductus arteriosus.

19. An apparatus for treating an anatomic defect in a heart, the apparatus comprising:
   an elongate catheter body having a proximal end and a distal end;
   a housing extending from the distal end of the catheter body for engaging tissues at a site of the anatomic defect;
   an energy transmission member adjacent to a distal end of the housing, the energy transmission member having at least one substantially planar surface, the housing being adapted to apply vacuum to the tissues to bring them together and position them against the energy transmission member; and
   a plurality of struts formed in a pattern, the struts being coupled to the housing,
   wherein the pattern in the plurality of struts includes at least one area of more closely positioned struts relative to another area of less closely positioned struts, such that different areas of the energy transmission member provide different amounts of energy transmission to the tissues.

20. An apparatus as in claim 19, wherein the energy transmission member comprises an outer rim extending at least partially around an outer circumference thereof, and
   wherein the plurality of struts are attached only to the outer rim and not to one another.

21. An apparatus for treating an anatomic defect in a heart, the apparatus comprising:
   an elongate catheter body having a proximal end and a distal end;
   a housing extending from the distal end of the catheter body for engaging tissues at a site of the anatomic defect;
   an energy transmission member adjacent to a distal end of the housing, the energy transmission member having at least one substantially planar surface, the housing being adapted to apply vacuum to the tissues to bring them together and position them against the energy transmission member; and
   a plurality of struts formed in a pattern, the struts being coupled to the housing,
   wherein the energy transmission member includes an outer rim extending at least partially around an outer circumference thereof, and
   wherein the plurality of struts are attached to the outer rim at between 8 and 16 attachment points to enhance collapsibility of the energy transmission member.

22. An apparatus as in claim 21, wherein the plurality of struts are attached only to the outer rim and not to one another.

* * * * *